(12) United States Patent
Nagatomi et al.

(10) Patent No.: US 9,046,490 B2
(45) Date of Patent: Jun. 2, 2015

(54) FLUORESCENCE DETECTION DEVICE

(71) Applicants: PANASONIC CORPORATION, Osaka (JP); SANYO Electric Co., Ltd., Osaka (JP)

(72) Inventors: Kenji Nagatomi, Osaka (JP); Masaya Nakatani, Hyogo (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 14/498,596

(22) Filed: Sep. 26, 2014

(65) Prior Publication Data

US 2015/0014552 A1    Jan. 15, 2015

Related U.S. Application Data

(63) Continuation of application No. PCT/JP2013/057463, filed on Mar. 15, 2013.

(30) Foreign Application Priority Data

Mar. 29, 2012  (JP) .................................. 2012-077899

(51) Int. Cl.
    *G01N 21/64* (2006.01)
(52) U.S. Cl.
    CPC ........ *G01N 21/6486* (2013.01); *G01N 21/6452* (2013.01); *G01N 2021/6463* (2013.01); *G01N 21/645* (2013.01)
(58) Field of Classification Search
    CPC .................................................. G01N 21/6486
    USPC .................................................. 250/545, 295
    See application file for complete search history.

(56) References Cited

U.S. PATENT DOCUMENTS

| 8,064,317 B2 * | 11/2011 | Nagatomi ................ 369/112.19 |
| 2009/0225645 A1 | 9/2009 | Nagatomi |
| 2010/0232282 A1 | 9/2010 | Nagatomi et al. |
| 2011/0075545 A1 | 3/2011 | Nagatomi et al. |

FOREIGN PATENT DOCUMENTS

| JP | 2001-238674 A | 9/2001 |
| JP | 2006-322707 A | 11/2006 |
| JP | 2009-063310 A | 3/2009 |
| JP | 2009-211770 A | 9/2009 |
| JP | 2010-211903 A | 9/2010 |
| JP | 2011-070752 A | 4/2011 |

OTHER PUBLICATIONS

International Search Report issued in Application No. PCT/JP2013/057463 dated Jun. 18, 2013.

* cited by examiner

*Primary Examiner* — David Porta
*Assistant Examiner* — Faye Boosalis
(74) *Attorney, Agent, or Firm* — McDermott Will & Emery LLP

(57) ABSTRACT

To provide a fluorescence detection device that can effectively remove autofluorescence using a simple configuration. A fluorescence detection device comprises: semiconductor laser for emitting excitation light; an objective lens for converging excitation light onto a sample on a biosensor substrate; an anamorphic lens which introduces astigmatism to fluorescence that is from the biosensor substrate and incident on the objective lens and that passed through the objective lens; a spectral element for separating the fluorescence into a plurality of light rays; and a fluorescence detector for receiving the light rays separated by the spectral element. On the light receiving surface of the fluorescence detector, the spectral element splits the fluorescence so that the fluorescence generated at the sample is separated from the fluorescence generated at a specific depth position other than the sample position.

8 Claims, 16 Drawing Sheets

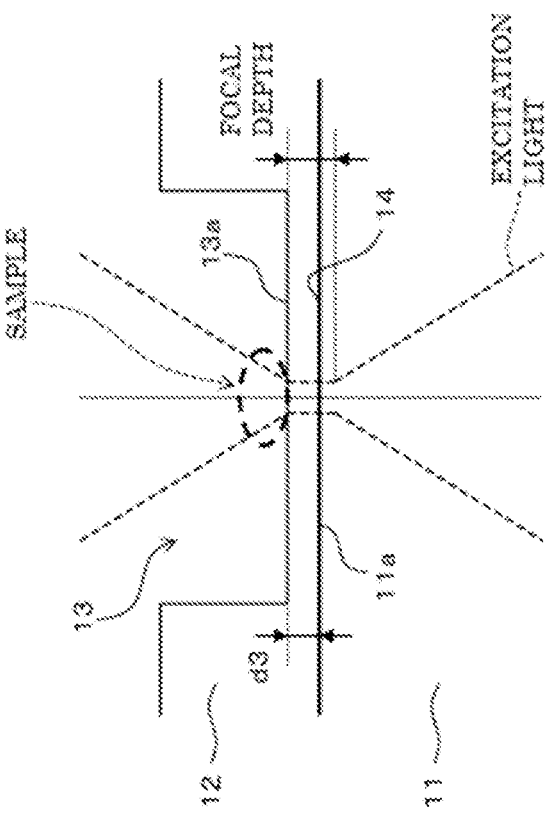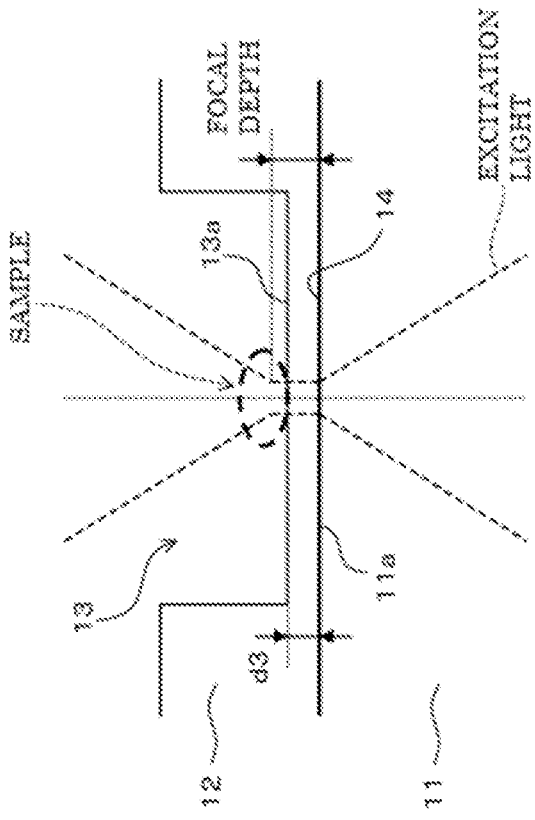

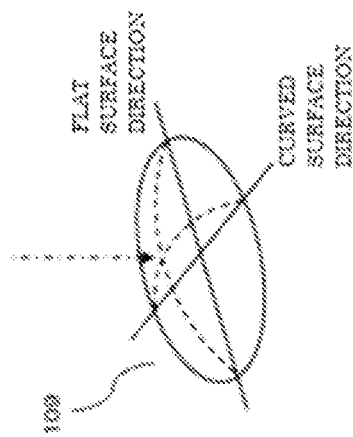
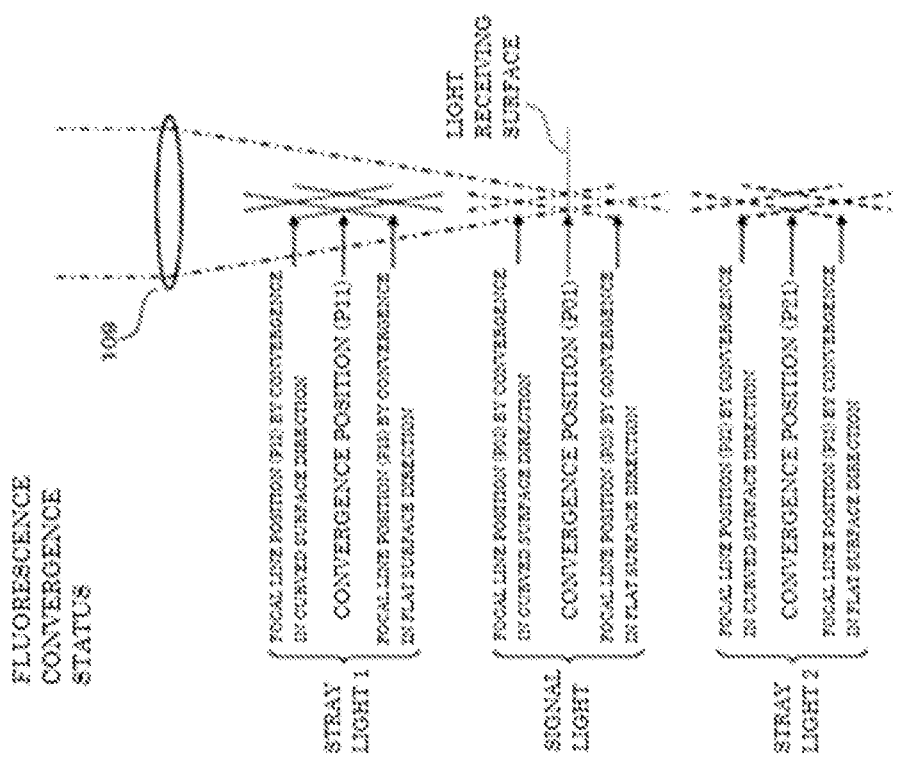
FIG. 5A
FIG. 5B

LIGHT RAY DIVISION PATTERN

SIGNAL LIGHT

STRAY LIGHT 1

STRAY LIGHT 2

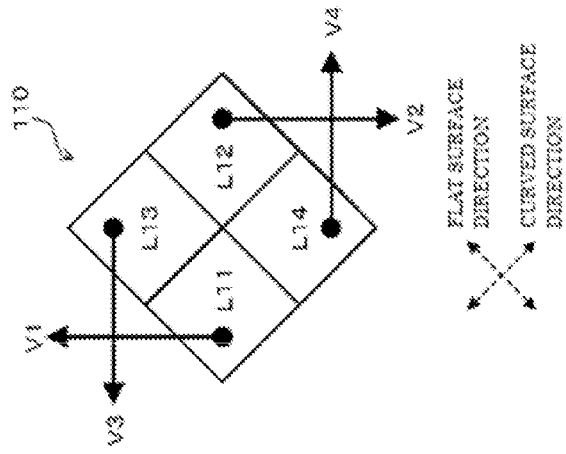
FIG. 9A  FIG. 9B  FIG. 9C
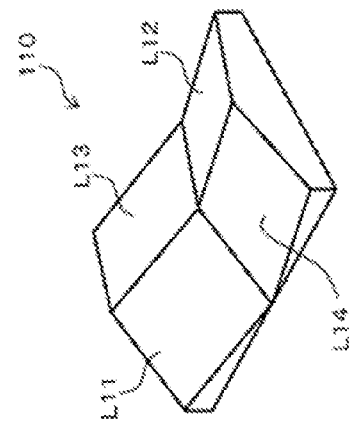
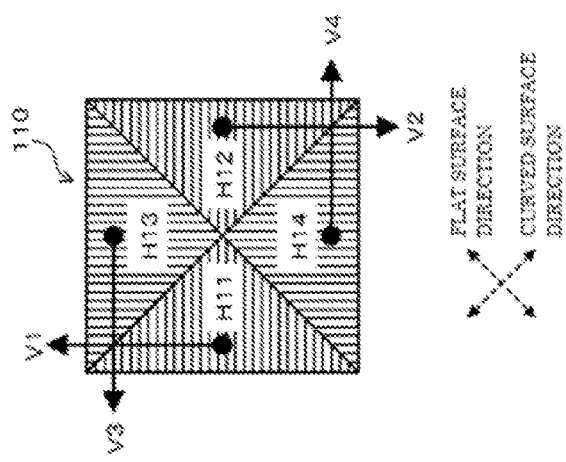
FIG. 9D
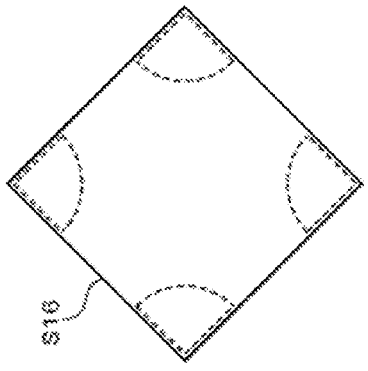
FIG. 9E
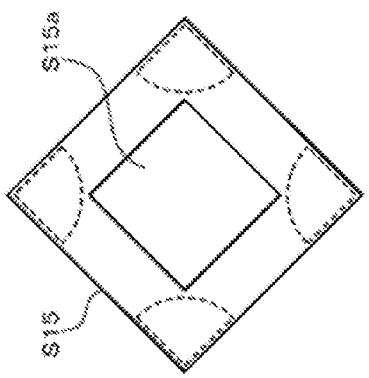
FIG. 9F
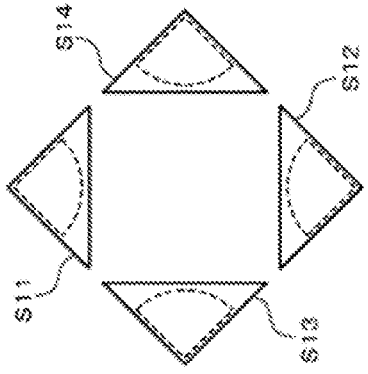

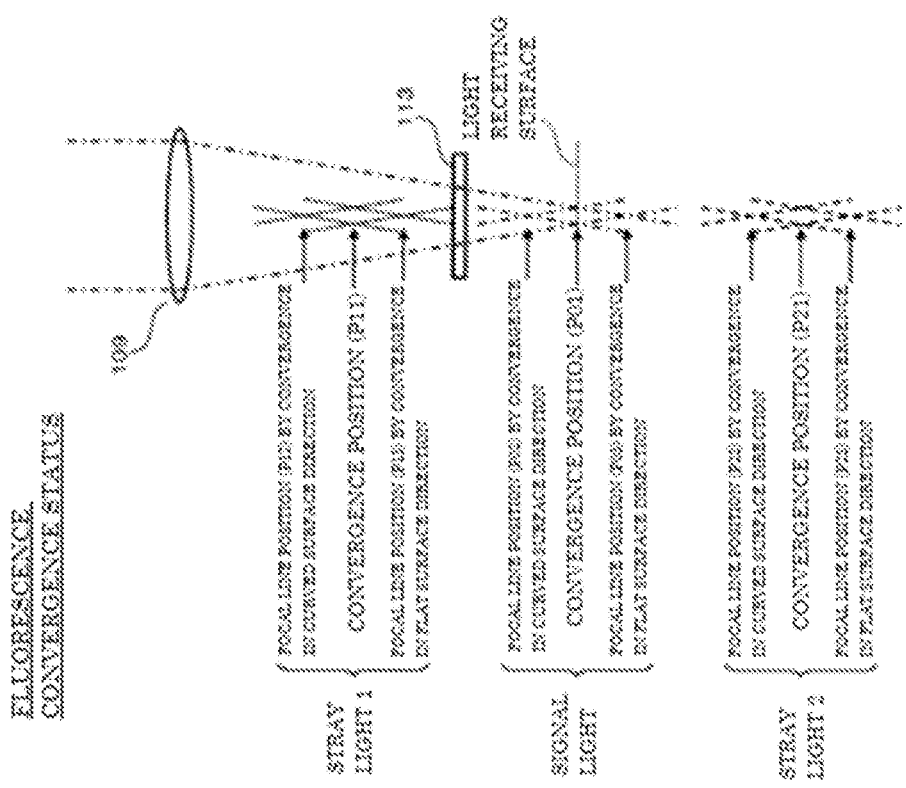
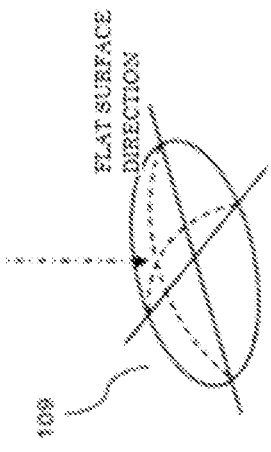
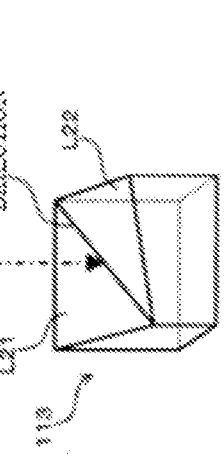
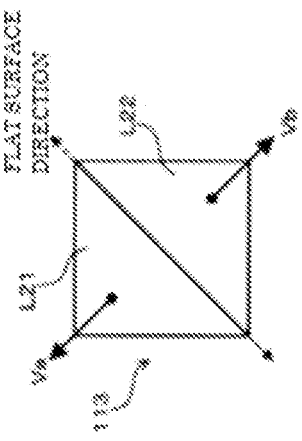
FIG. 10A
FIG. 10B
FIG. 10C
FIG. 10D

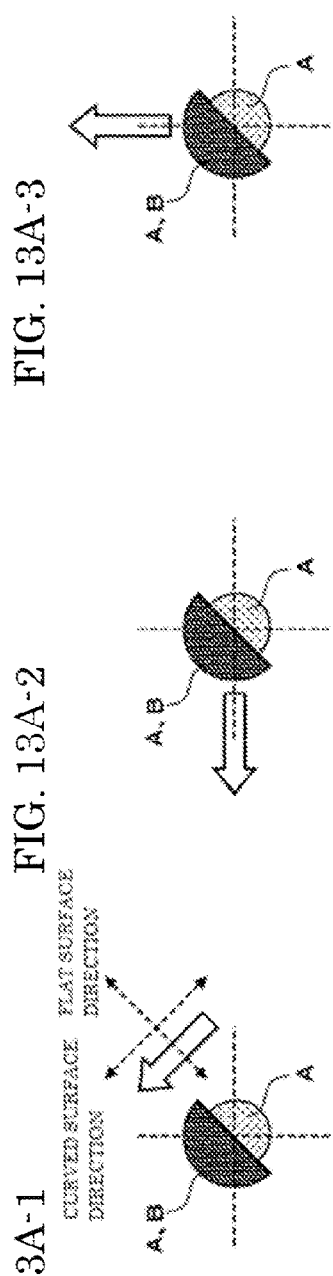
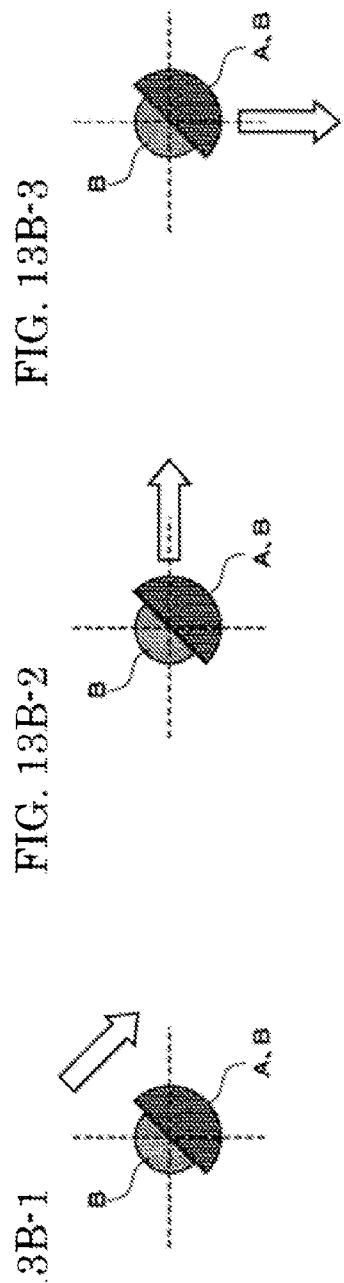
FIG. 13A-1  FIG. 13A-2  FIG. 13A-3
FIG. 13B-1  FIG. 13B-2  FIG. 13B-3
FIG. 13C-1  FIG. 13C-2  FIG. 13C-3

FLUORESCENCE DETECTION DEVICE

RELATED APPLICATIONS

The present application is a continuation of U.S. National Phase PCT/JP2013/057463, filed Mar. 15, 2013, which claims priority from Japanese Patent Application No. 2012-077899 filed Mar. 29, 2012, the entire disclosures of which are incorporated herein by reference for all purposes.

TECHNICAL FIELD

The present invention relates to a fluorescence detection device for irradiating excitation light to a sample adjusted by fluorescence-labeling a test object (e.g., cell) to thereby detect fluorescence generated from the sample.

BACKGROUND ART

In recent years, various techniques have been suggested to automate the detection of a fluorescently-labeled sample. For example, Japanese Patent Unexamined Publication No. 2001-238674 suggests a DNA disk using an existing optical disk technique. According to this technique, a series of spots are formed to be arranged on the disk in a spiral manner and a track is formed along the arranged spots and an address mark is formed on this track. Light is scanned along the track and the fluorescence generated from the spot due to this light is detected by a light detector.

Japanese Patent Unexamined Publication No. 2001-238674 also discloses a configuration to remove fluorescence generated at a region other than the spot (so-called outside-region fluorescence or autofluorescence). When light passes through a disk substrate or other optical members for example, the outside-region fluorescence or autofluorescence occurs. When such autofluorescence enters a light detector, a risk is caused where a lowered accuracy is caused to detect the fluorescence generated from a sample existing in the spot. In order to suppress such a disadvantage, Japanese Patent Unexamined Publication No. 2001-238674 discloses a configuration in which an aperture is placed in a front stage of the light detector to converge the fluorescence generated due to the sample at an opening section of the aperture to thereby remove unnecessary fluorescence such as outside-region fluorescence or autofluorescence.

SUMMARY OF THE INVENTION

Technical Problems

However, in the case of Japanese Patent Unexamined Publication No. 2001-238674 described above, the opening section must be accurately positioned at a position to converge the fluorescence generated due to a sample, thus causing a disadvantage of a difficult position adjustment of the opening section for example. If the size of the opening section is increased in order to simplify the position adjustment on the other hand, an increased ratio is caused at which autofluorescence passes through the opening section, thus failing to effectively suppress a lowered detection accuracy due to autofluorescence. Furthermore, fluorescence generated from a position other than a position accommodating a target sample (i.e., outside-region fluorescence) is also caused, thus resulting in a lowered accuracy to detect the fluorescence generated from a target sample.

The present invention has been made in view of the points as described above. It is an objective of the invention to provide a fluorescence detection device that can effectively remove, with a simple configuration, unnecessary fluorescence generated from a sample other than a target sample (e.g., autofluorescence or outside-region fluorescence).

Solution to Problems

An embodiment of the present invention relates to a fluorescence detection device that irradiates a sample holding carrier for holding a fluorescently-labeled sample with irradiation light and detects fluorescence yielded from the sample irradiated with the irradiation light. The fluorescence detection device according to this embodiment includes: a light source that emits the irradiation light; an objective lens that converges the irradiation light at the sample on the sample holding carrier; an astigmatism element for introducing astigmatism to fluorescence having entered the objective lens from the sample holding carrier and having passed through the objective lens; a spectral element for separating the fluorescence into a plurality of light rays and a fluorescence detector for receiving the light ray separated by the spectral element. The spectral element disperses the fluorescence on the light receiving surface of the light detector so that the fluorescence generated from the sample position is separated from the fluorescence generated from a specific depth position other than the sample position. The fluorescence detector has a light-receiving section in a region in which the fluorescence generated from the sample position is irradiated and that the fluorescence generated from the specific depth region other than the sample position is not irradiated.

According to the fluorescence detection device of this embodiment, the light receiving surface of the fluorescence detector has thereon the fluorescence generated from the sample position not superposed with the fluorescence generated from the specific depth region other than the sample position. (so-called autofluorescence). Thus, the light-receiving section provided in the region irradiated only with the fluorescence generated from the sample position can receive only the fluorescence generated from the sample position. This allows, by a simple configuration, the fluorescence generated from the sample position to be accurately detected by removing autofluorescence.

In the fluorescence detection device according to this embodiment, the astigmatism element generates a first focal line by the fluorescence convergence in a first direction and generates a second focal line by the fluorescence convergence in a second direction vertical to the first direction. The spectral element may be configured so as to separate four of the light rays from the fluorescence so that, when an intersection point of two straight lines that are parallel to the first direction and the second direction, respectively, and that intersect to each other is aligned to an optical axis of the fluorescence, four of the light rays are included in four fluorescence regions divided by the two straight lines, respectively. As described above, a region to be dispersed by the spectral element can be set based on the direction in the astigmatism direction to separate the fluorescence generated from the sample from the fluorescence generated from a specific depth position other than the sample so that the former is not superposed with the latter on the fluorescence detector.

In this case, the spectral element may be configured to have a structure that changes traveling directions of four of the light rays so that four of the light rays are respectively irradiated to four apex angles of a square on the fluorescence detector. This structure can provide a compact region irradiated only with the fluorescence generated from the sample position, thus providing the light-receiving section with a simple layout configuration.

Also according to the fluorescence detection device according to this embodiment, the astigmatism element generates a first focal line by the fluorescence convergence in a first direction and generates a second focal line by the fluorescence convergence in a second direction vertical to the first direction. The spectral element is configured to separate two of the light rays from the fluorescence and is configured so that, when a straight line parallel to the first direction is aligned to an optical axis of the fluorescence, two of the light rays are included in two fluorescence regions divided by the straight line, respectively. In this case, the spectral element is provided closer to the objective lens than the objective lens-side focal line among two focal lines generated by the conversion by the astigmatism element of the fluorescence generated from the sample position. As described above, by setting a region to be dispersed by the spectral element based on the direction with the astigmatism direction, the fluorescence generated from the sample can be separated from the fluorescence generated from a depth position other than the sample on the light detector so that the former is not superposed with the latter. Also according to this configuration, the spectral element can have a simpler configuration when compared with a case where there are four light rays to be splitted.

In this case, the spectral element is configured to have a structure that changes traveling directions of two of the light rays so that two of the light rays are separated from each other in the second direction. This configuration provides a compact region irradiated only with the fluorescence generated from the sample position, thus providing the light-receiving section with a simple layout configuration.

Also according to the fluorescence detection device according to this embodiment, the sample holding carrier may be configured to include: a sample accommodation unit for storing the sample; and a reflecting surface that is provided closer to the incidence side of the irradiation light than the sample accommodation unit and that reflects a part of the irradiation light. The spectral element is configured by a wavelength-selective diffraction element. The spectral element is configured to receive the fluorescence and reflection light of the irradiation light reflected by the reflecting surface. The spectral element is also configured to further give to the fluorescence a diffraction action for separating, based on a wavelength difference between the fluorescence and the reflection light, the fluorescence and the reflection light from each other. This configuration allows one light detector to receive the fluorescence and reflection light of the irradiation light reflected by the reflecting surface, thus achieving a reduced number of components and a simpler configuration.

Effect of the Invention

According to the present invention, a fluorescence detection device can be provided that may effectively remove autofluorescence by a simple configuration.

The effect or significance of the present invention will be clearer from the following description of an embodiment. However, the following embodiment is merely one illustration for carrying out the present invention. Thus, the present invention is not limited in any way by the following embodiment.

BRIEF DESCRIPTION OF THE DRAWINGS

FIGS. 3A and 3B illustrate a focal depth of excitation light according to Embodiment 1.

FIG. 5A is a schematic view illustrating the fluorescence convergence status according to the technical principle of Embodiment 1 and FIG. 5B is the configuration of an anamorphic lens.

FIGS. 9A to 9F illustrate a configuration example of a spectral element according to Embodiment 1 and illustrate the configuration of a sensor provided on a light receiving surface of a fluorescence detector.

FIG. 10A is a diagram illustrating the fluorescence convergence status according to the technique principle of Embodiment 2, FIG. 10B is a schematic view illustrating the configuration of the anamorphic lens, FIG. 10C is a perspective view illustrating the shape of a spectral element, and FIG. 10D is a diagram illustrating a spectral element seen from the light incidence side.

FIGS. 13A-1 to 13C-3 illustrate a modification example of the fluorescence light ray region on the light receiving surface of the fluorescence detector according to Embodiment 2.

DESCRIPTION OF EMBODIMENTS

The following section will describe an embodiment of the present invention with reference to the drawings.

Embodiment 1

Figure 1A:
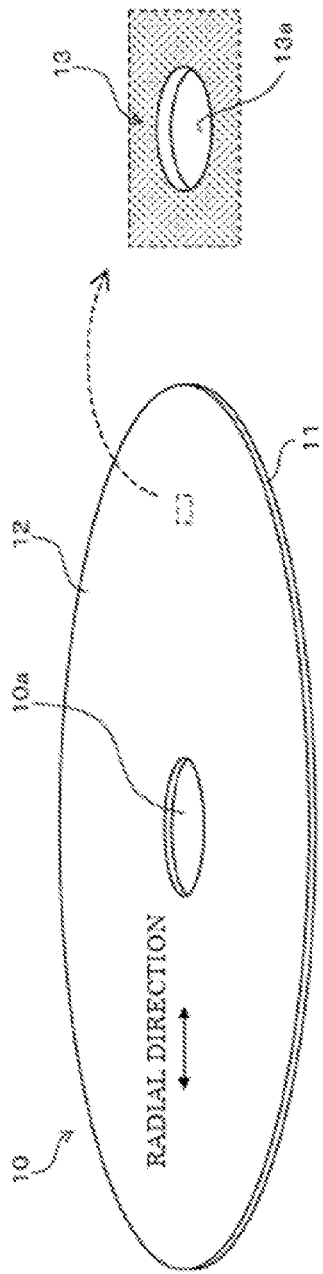
FIG. 1A is a perspective view schematically illustrating the configuration of the appearance of a biosensor substrate according to Embodiment 1.

FIG. 1A is a perspective view schematically illustrating the appearance of biosensor substrate 10 used in Embodiment 1.

Biosensor substrate 10 is used to detect erythrocytes infected with malarial parasites in human blood for example.

Biosensor substrate 10 has a disk-like shape as in an optical disk (e.g., CD DVD) and has a circular hole 10a at the center thereof. Biosensor substrate 10 has a structure in which well layer 12 is layered on an upper face of base substrate 11. Well layer 12 includes, as shown by the enlarged view of FIG. 1A shown at the right end, minute wells 13 composed of columnar dents. Wells 13 are arranged from the inner circumference to the outer circumference of biosensor substrate 10 in a concentric or spiral manner. Well 13 has bottom face 13a having a depth lower than the upper face of well layer 12. Bottom face 13a has a diameter and a height set so that bottom face 13a can accommodate a sample when the sample is dripped therein.

Figure 1B:
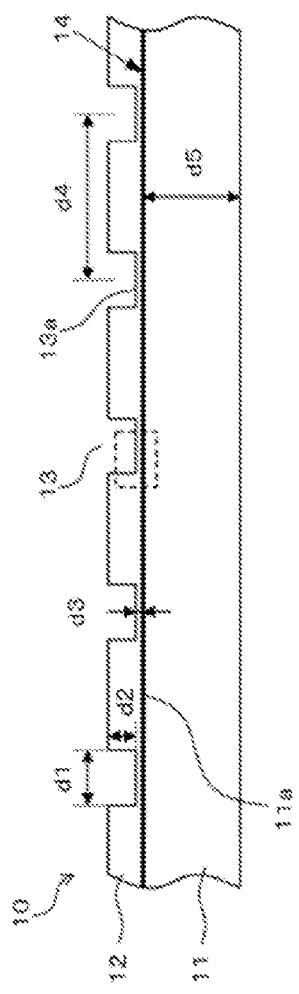
FIG. 1B is a cross-sectional view illustrating the biosensor substrate cut in a plane vertical to a plane.
Figure 1C:
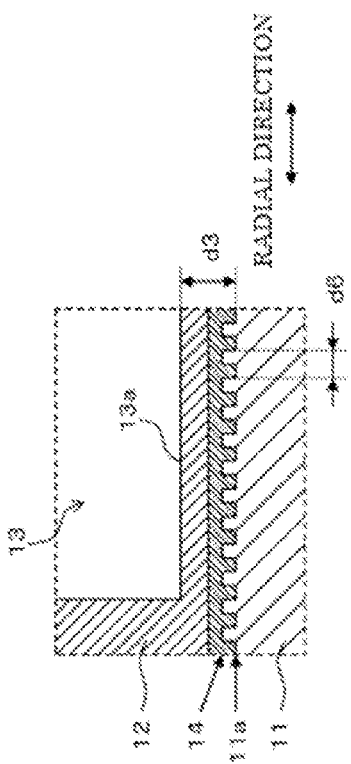
FIG. 1C is a partial enlarged view illustrating the cross section of the biosensor substrate.

FIG. 1B is a cross-sectional view illustrating biosensor substrate 10 cut in a plane vertical to a plane. FIG. 1C is an enlarged view illustrating a part shown by the broken line of FIG. 1B.

Base substrate 11 has, at the upper side (well layer 12-side), a spiral track (pit row) as in an optical disk. The pit retains address information for identifying a position on a surface of biosensor substrate 10. As in the case of CD and DVD, the track is scanned by excitation light (which will be described later) at a fixed line velocity to thereby reproduce address information. Base substrate 11 and well layer 12 have therebetween reflection film 14. The existence of reflection film 14 layered on the upper face of base substrate 11 provides reflecting surface 11a on the upper face of base substrate 11. Reflecting surface 11a functions as an interface between reflection film 14 and base substrate 11. Wells 13 are formed at the upper face side of well layer 12 to have a specific interval thereamong. Well 13 has bottom face 13a positioned slightly above reflection film 14 to thereby provide a space between bottom face 13a of well 13 and the upper face of reflection film 14.

It is assumed that well 13 has diameter d1 and height d2, bottom face 13a and reflecting surface 11a have therebetween interval d3, wells 13 have thereamong interval d4, base substrate 11 has thickness d5, and reflecting surface 11a has track pitch d6. In Embodiment 1, diameter d1 and height d2 are set to 100 μm and 50 μm, respectively. Intervals d3 and d4 are set to 2 μm and 300 μm, respectively. Thickness d5 is set to 0.6 mm. Track pitch d6 is set to 1 μm. Reflection film 14 has reflectivity of 3 to 4% to excitation light (which will be described later).

Figure 2:
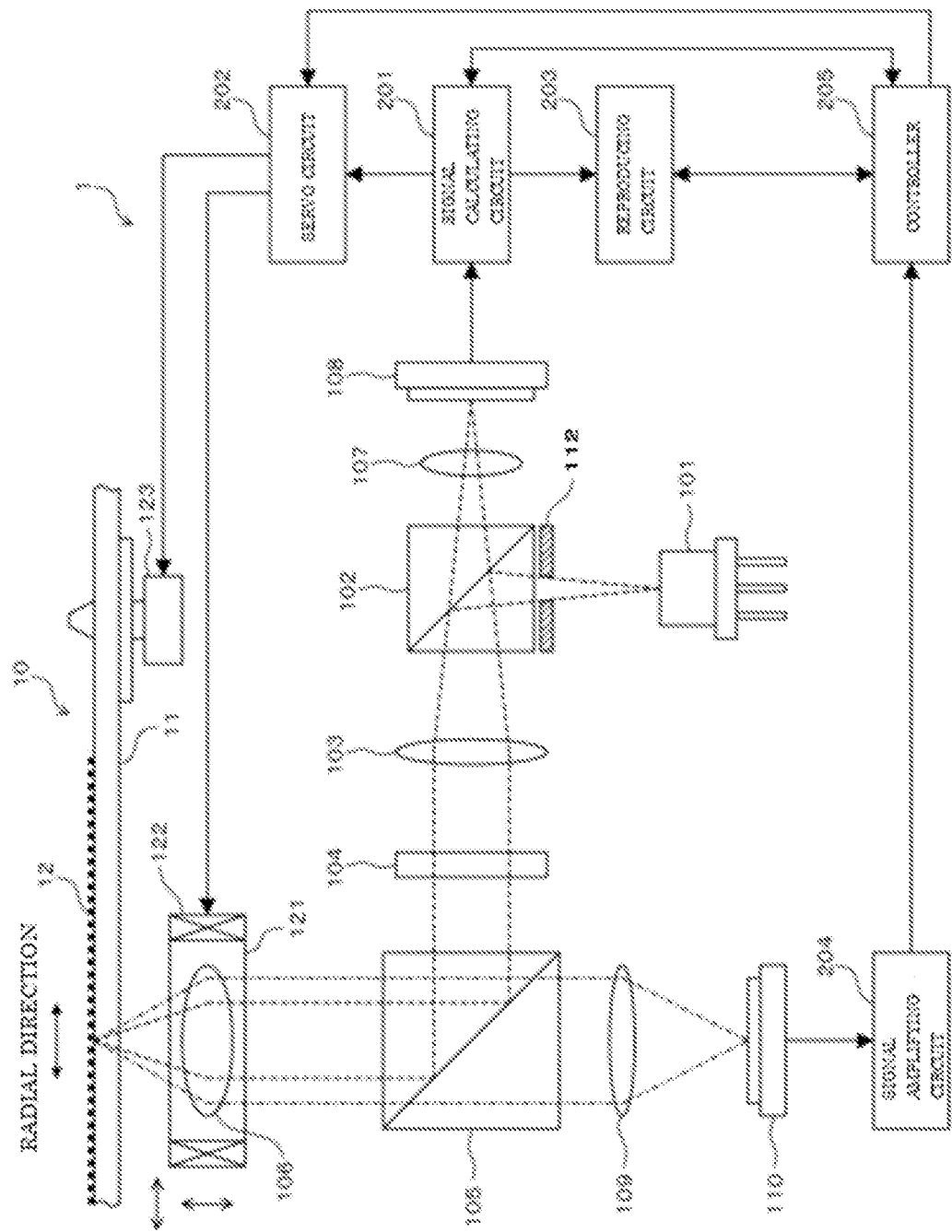
FIG. 2 illustrates the configuration of the fluorescence detection device according to Embodiment 1.

FIG. 2 illustrates a configuration of fluorescence detection device 1 according to Embodiment 1. Fluorescence detection device 1 is used to determine, for example, whether or not erythrocytes stored in well 13 of biosensor substrate 10 are infected with malarial parasites.

Prior to the use of fluorescence detection device 1, a sample prepared by fluorescently-labeling a test object is stored in well 13 of biosensor substrate 10 in advance. In Embodiment 1, a test object is an erythrocyte having a diameter of about 10 μm and a thickness of about 2 μm. When the erythrocyte is infected with malarial parasites, the interior thereof is fluorescently-labeled. Then, the infected erythrocyte and a not-infected erythrocyte are parallelly arranged on bottom faces 13a of wells 13 having a diameter of 100 μm. Then, holes 10a of biosensor substrate 10 (see FIG. 1A) storing therein the samples as described above are set on a rotation device 123 (turn table) of fluorescence detection device 1 and measurement is started.

An optical system of the fluorescence detection device 1 includes: semiconductor laser 101; polarization beam splitter (PBS) 102; collimator lens 103; ¼ wavelength plate 104; dichroic prism 105; objective lens 106; anamorphic lens 107; light detector 108; anamorphic lens 109; spectral element 110; fluorescence detector 111; and aperture 112. Fluorescence detection device 1 includes, in addition to the above optical system, holder 121, objective lens actuator 122, rotation device 123, signal calculating circuit 201, servo circuit 202, reproducing circuit 203, signal amplifying circuit 204, and controller 205.

Semiconductor laser 101 emits laser light having a wavelength of about nm (hereinafter referred to as "excitation light"). Excitation light in Embodiment 1 is an example of irradiation light described in claims. FIG. 2 shows, by the broken line, excitation light emitted from semiconductor laser 101 that is guided to biosensor substrate 10 (i.e., excitation light passing through aperture 112). Aperture 112 includes a circular opening having a specific aperture. Aperture 112 limits the aperture of excitation light. Semiconductor laser 101 is positioned so that excitation light emitted from semiconductor laser is S-polarized to PBS 102. By this configuration, the excitation light emitted from semiconductor laser 101 is caused by aperture 112 to have a limited aperture and is subsequently reflected by PBS 102, thereby entering collimator lens 103.

Upon receiving the excitation light from PBS 102, collimator lens 103 converts the excitation light to parallel light. Consequently, the excitation light having passed through collimator lens 103 is turned into parallel light having a specific diameter. ¼ wavelength plate 104 receives the excitation light from collimator lens 103 and converts the excitation light to circularly-polarized light and receives excitation light from dichroic prism 105 and converts the excitation light to straightly-polarized light orthogonal to the direction along which light received from collimator lens 103 is polarized. As a result, the excitation light coming from collimator lens 103 to PBS 102 passes through PBS 102.

Dichroic prism 105 is configured to reflect laser light having a wavelength of about 405 nm and to allow laser light having a wavelength of about 450 to 540 nm to go therethrough. Thus, excitation light received from ¼ wavelength plate 104 is reflected by dichroic prism 105 and enters objective lens 106.

Objective lens 106 is configured to appropriately converge excitation light to biosensor substrate 10. Specifically, objective lens 106 is configured to converge excitation light received from dichroic prism 105 to have a specific NA (which means the number of openings and which is 0.34 in this case). Excitation light enters objective lens 106 at an incidence aperture determined by an aperture of aperture 112. Excitation light converged by objective lens has a focal depth determined by the NA of the excitation light. The focal depth of the excitation light will be described later with reference to FIGS. 3A and 3B.

Objective lens 106 is driven, while being held by holder 121, by objective lens actuator 122 in a focus direction (a direction vertical to biosensor substrate 10) and a tracking direction (a diameter direction of biosensor substrate 10). Specifically, objective lens 106 is driven so that excitation light follows a track composed of pit rows while being in focus on reflecting surface 11a of biosensor substrate 10. The excitation light focused on reflecting surface 11a is partially reflected by reflecting surface 11a and most of the excitation light passes through reflecting surface 11a. The excitation light reflected by reflecting surface 11a will be hereinafter referred to as "reflected excitation light". As will be described later, a servo signal is generated to drive, based on this reflected excitation light, objective lens 106 in the focus direction and the tracking direction (see FIG. 4).

FIGS. 3A and 3B illustrate a focal depth of excitation light.

As described above, the excitation light has a wavelength of 405 nm and the excitation light has NA (the number of openings) of 0.34. Generally, the focal depth can be calculated by wavelength/(NA×NA). Thus, the excitation light of Embodiment 1 has a focal depth of about 3.5 μm. Bottom face 13a and reflecting surface 11a have therebetween interval d3 set to be smaller than the focal depth of the excitation light and is set to 2.0 μm in this case.

As described above, when the NA of the excitation light is set, a spot diameter at a focal point position is about 1 μm. Track pitch interval d6 shown in FIG. 1C is set to 1 μm so as to be substantially equal to the above spot diameter.

FIG. 3A shows that the lowest point of the focal depth range of the excitation light is aligned with reflection film 14. FIG. 3B shows that the highest point of the focal depth range of the excitation light is aligned with bottom face 13a. By adjusting an offset voltage outputted from servo circuit to objective lens actuator 122, the focal depth range of the excitation light can be set to any of the statuses of FIGS. 3A and 3B.

In the statuses of FIGS. 3A and 3B, bottom face 13a of well 13 and reflecting surface 11a have therebetween interval d3 of 2 μm and the excitation light has a focal depth of 3.5 μm. Thus, bottom face 13a and reflecting surface 11a are both included in the focal depth range of the excitation light. Thus, when the focal point position of the excitation light is positioned on reflecting surface 11a by a focus servo, a sample provided on bottom face 13a is also focused.

Returning to FIG. 2, among the excitation light irradiated to biosensor substrate 10, the reflected excitation light reflected by reflecting surface 11a is reflected by dichroic prism 105 and is converted by ¼ wavelength plate 104 to straightly-polarized light and is converted by collimator lens 103 to convergent light. Then, reflected excitation light sent from collimator lens 103 to PBS 102 passes through PBS 102 as described above.

Anamorphic lens 107 introduces astigmatism to reflected excitation light received from PBS 102. The reflected excitation light having passed anamorphic lens 107 is received by light detector 108. Light detector 108 has a tetrameric sensor to receive reflected excitation light onto a light receiving surface. A detection signal of light detector 108 is inputted to signal calculating circuit 201.

Among the excitation light irradiated to biosensor substrate 10, the excitation light having passed reflecting surface 11a reaches bottom face 13a of well 13. When fluorescently-labeled erythrocytes infected with malarial parasites, which are parallelly arranged on bottom face 13a, are irradiated with excitation light, the malarial parasites generate fluorescence. This fluorescence has, as shown by the chain line in FIG. 2, NA (the number of openings) higher than that of the excitation light. Thus, objective lens 106 and dichroic prism 105 have therebetween fluorescence having a beam diameter larger than that of the excitation light. The fluorescence has NA of 0.65 for example. The fluorescence has a wavelength different from that of the excitation light and has a wavelength of 450 to 540 nm in Embodiment 1. On the other hand, erythrocytes not infected with malarial parasites are not fluorescently-labeled and thus do not generate fluorescence. In the manner as described above, erythrocytes infected with malarial parasites can be discriminated from erythrocytes not infected with malarial parasites.

The fluorescence sent from objective lens 106 to dichroic prism 105 passes through dichroic prism 105. Anamorphic lens 109 introduces astigmatism to the fluorescence received from dichroic prism 105. Spectral element 110 changes the traveling direction of the fluorescence in which astigmatism was introduced by anamorphic lens 109. Fluorescence detector has a sensor to receive the fluorescence whose traveling direction was changed by spectral element 110. Fluorescence detector 111 inputs a detection signal to signal amplifying circuit 204. Anamorphic lens 109, spectral element 110, and a sensor on the light receiving surface of fluorescence detector 111 will be described later with reference to FIG. 5A to FIG. 9F.

Signal calculating circuit 201 generates focus error signal FE and tracking error signal TE (which will be described later) based on the detection signal from light detector 108 and generates reproduced RF signal (which will be described later) based on the detection signal from light detector 108. Servo circuit 202 uses focus error signal FE and tracking error signal TE outputted from signal calculating circuit 201 to control the driving of objective lens actuator 122. Servo circuit 202 controls rotation device 123 using reproduced RF signal outputted from signal calculating circuit 201 so that biosensor substrate 10 is rotated at a fixed line velocity. Reproducing circuit 203 demodulates the reproduced RF signal outputted from signal calculating circuit to generate reproduction data. Signal amplifying circuit 204 amplifies the detection signal from fluorescence detector 111.

Controller 205 controls, in addition to signal calculating circuit 201, servo circuit 202, and reproducing circuit 203, the respective parts of fluorescence detection device 1. Based on reproduction data (address information) outputted from reproducing circuit 203 and a signal outputted from signal amplifying circuit 204, controller 205 determines a position in biosensor substrate 10 at which fluorescence in well 13 was detected. Then, address information corresponding to well 13 in which fluorescence was detected is retained in an internal memory.

Figure 4:
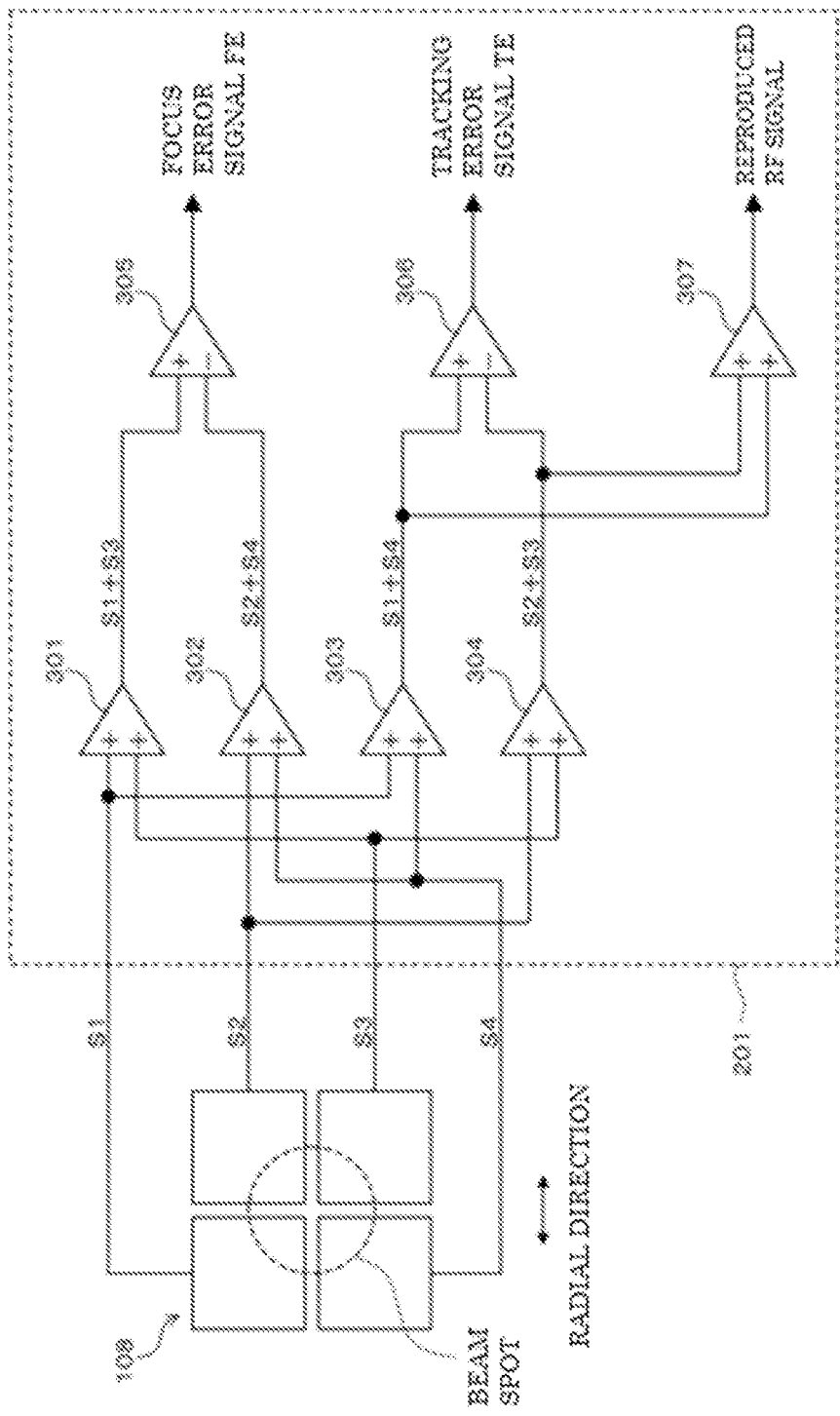
FIG. 4 illustrates a circuit configuration of a signal calculating circuit according to Embodiment 1.

FIG. 4 illustrates a circuit configuration of signal calculating circuit 201.

Light detector 108 has a tetrameric sensor for receiving reflected excitation light on the light receiving surface as described above. The tetrameric sensor has, at the upper-left, upper-right, lower-right, and lower-left positions thereof, sensors that output detection signals S1 to S4 based on the beam spots of the received reflected excitation lights, respectively. On the light receiving surface of light detector 108 of FIG. 4, a direction corresponding to the radial direction of the disk (diameter direction) is a left-and-right direction. Focus error signal FE and tracking error signal TE are generated based on the astigmatism method and the one beam push pull method used in an existing optical disk device.

Signal calculating circuit 201 includes adders 301 to 304, and 307 and subtractors 305 and 306. Adder 301 outputs a signal obtained by adding detection signals S1 and S3 to subtractor 305. Adder 302 outputs a signal obtained by adding detection signals S2 and S4 to subtractor 305. Adder 303 outputs a signal obtained by adding detection signals S1 and S4 to subtractor and adder 307. Adder 304 outputs a signal obtained by adding detection signals S2 and S3 to subtractor 306 and adder 307.

Subtractor 305 subtracts the output signals of adders 301 and 302 to output focus error signal FE. Subtractor 306 subtracts the output signals of adders 303 and 304 to output tracking error signal TE. Adder 307 adds the output signals of adders 303 and 304 to output a reproduced RF signal. Specifically, focus error signal FE, tracking error signal TE, and reproduced RF signal can be acquired by calculating the following formulae (1) to (3).

$$FE=(S1+S3)-(S2+S4) \quad (1)$$

$$TE=(S1+4)-(S2+S3) \quad (2)$$

$$RF=(S1+S2+S3+S4) \quad (3)$$

When the focal point position of objective lens 106 is positioned on reflecting surface 11a, the beam spot on the tetrameric sensor of light detector forms a circle of least confusion, resulting in focus error signal FE in the above formula (1) having a value of 0. When the focal point position of objective lens 106 is positioned just above a track (pit) of reflecting surface 11a, the beam spot on the tetrameric sensor of light detector 108 is equally formed over two left sensors and two right sensors, thus resulting in tracking error signal TE in the above formula (2) having a value of 0.

As shown in FIGS. 3A and 3B, even when a sample is position on the focal point position of objective lens 106, fluorescence entering fluorescence detector 111 is not always limited to fluorescence generated from the sample. Specifically, fluorescence generated from a position dislocated in an optical axis direction with regard to the sample (so-called autofluorescence) also enters fluorescence detector 111. The autofluorescence as described above is generated when excitation light passes an optical component such as objective lens 106 or biosensor substrate 10 and is also generated from a sample existing at a position other than the convergence position of excitation light. When autofluorescence enters fluorescence detector 111, a disadvantage of a lowered detection accuracy of fluorescence detector 111 is caused for example.

To prevent this, in Embodiment 1, anamorphic lens 109 and spectral element 110 are used to extract, from among fluorescence entering fluorescence detector 111, only fluorescence generated from a sample at an excitation light convergence position. The following section will describe the technical principle as described above with reference to FIG. 5A to FIG. 8B.

FIG. 5A illustrates a fluorescence convergence status. FIG. 5A illustrates convergence statuses of fluorescence generated from a sample (hereinafter referred to as "signal light"), fluorescence generated from a position deeper than the sample in an optical axis direction (hereinafter referred to as "stray light 1"), and fluorescence generated from a position shallower than the sample in the optical axis direction (hereinafter referred to as "stray light 2").

FIG. 5B is a schematic view illustrating the configuration of anamorphic lens 109. Anamorphic lens 109 applies, to fluorescence entering in a direction parallel to the lens optical axis, a converge action in a curved surface direction and a flat surface direction. The curved surface direction and the flat surface direction are orthogonal to each other. The curved surface direction has a smaller curvature radius than that in the flat surface direction and is effective to converge fluorescence entering anamorphic lens 109.

For brief description of an astigmatism action in anamorphic lens 109, the terms "curved surface direction" and "flat surface direction" are used for convenience. However, anamorphic lens 109 may provide an action connecting a focal line at different positions on the lens optical axis. Thus, the anamorphic lens in the "flat surface direction" of FIG. 5B is not shown as having a shape having a flat surface. In Embodiment 1, it is assumed that fluorescence enters anamorphic lens 109 as parallel light. However, when anamorphic lens 109 receives fluorescence in a convergence status, anamorphic lens 109 in the "flat surface direction" may have a straight shape (curvature radius=∞). Anamorphic lens 109 also may be configured by a plurality of lenses such as a cylindrical lens or a light-gathering lens for example.

With reference to FIG. 5A, signal lights converged by anamorphic lens are caused, by the conversions in the curved surface direction and the flat surface direction, to connect focal lines at different positions, respectively. Focal line position (P02) by the conversion in the curved surface direction is closer to anamorphic lens 109 than focal line position (P03) by the conversion in the flat surface direction. Signal light convergence position (P01) is between an intermediate position of focal line positions (P02) and (P03) by the convergence in the curved surface direction and the flat surface direction. When excitation light is in a focus status, a signal light beam forms a circle of least confusion at convergence position (P01). At convergence position (P01), a light receiving surface of fluorescence detector 111 is arranged to be vertical to the optical axis of fluorescence entering anamorphic lens 109.

Stray light 1 converged by anamorphic lens 109 similarly has focal line position (P12) by the conversion in the curved surface direction closer to anamorphic lens 109 than focal line position (P13) by the convergence in the flat surface direction. Anamorphic lens 109 is designed so that focal line position (P13) by the convergence of stray light 1 in the flat surface direction is closer to anamorphic lens 109 than signal light convergence position (P01).

Stray light 2 converged by anamorphic lens 109 similarly has focal line position (P22) by the convergence in the curved surface direction closer to anamorphic lens 109 than focal line position (P23) by the convergence in the flat surface direction. Anamorphic lens 109 is designed so that focal line position (P22) by the convergence of stray light 2 in the curved surface direction is farther from anamorphic lens 109 than signal light convergence position (P01).

In view of the above, the following section will describe the relation among signal light and light ray regions of stray lights 1 and 2 on a light receiving surface of fluorescence detector 111.

Figure 6A:
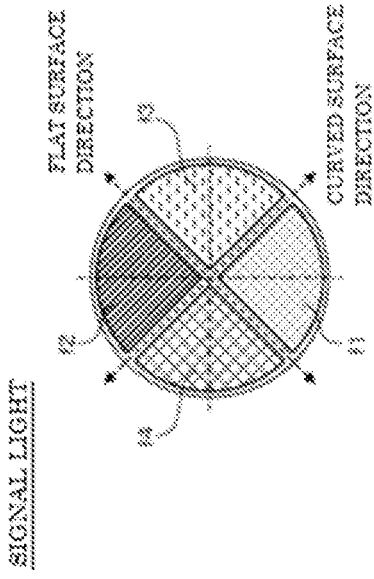
FIGS. 6A to 6D illustrate the distribution status of a light ray region according to the technique principle of Embodiment 1.

FIG. 6A illustrates four light ray regions f1 to f4 set in fluorescence entering anamorphic lens 109. FIG. 6A illustrates fluorescence seen in the traveling direction along which the fluorescence enters anamorphic lens 109.

Figure 6B:
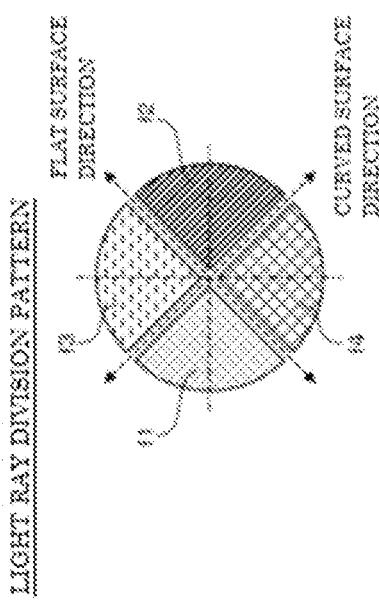
Figure 6C:
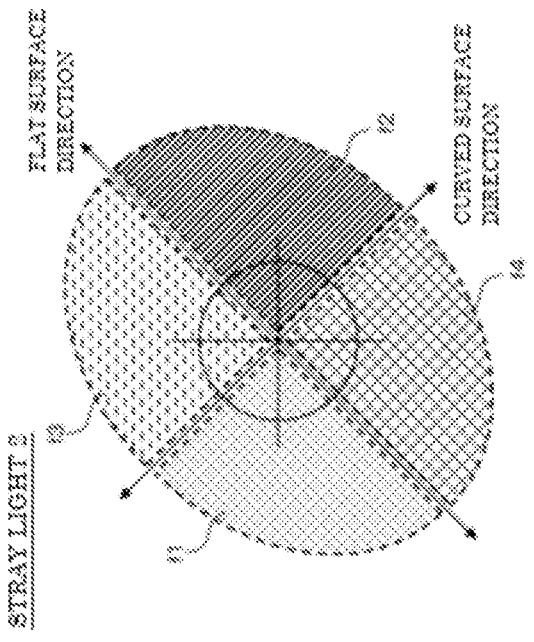
Figure 6D:
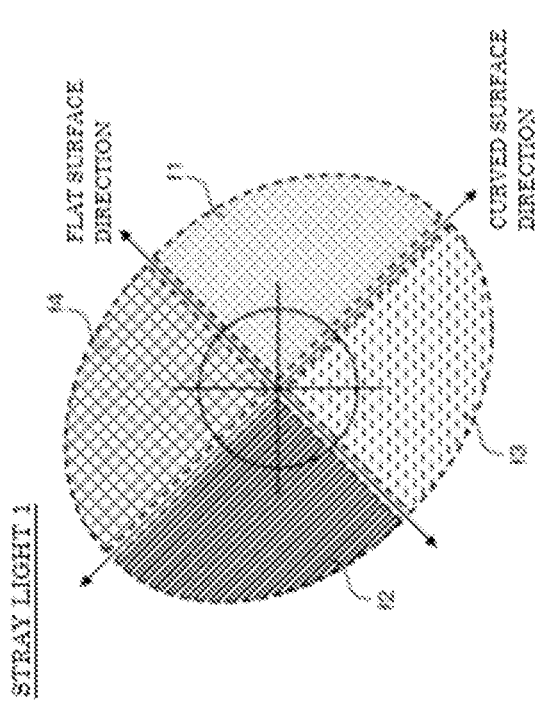
Figure 7A:
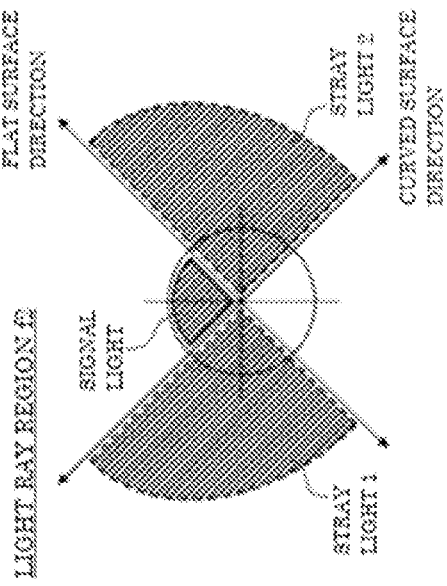
FIGS. 7A to 7D illustrate the distribution of signal light and stray light according to the technique principle of Embodiment 1.
Figure 7B:
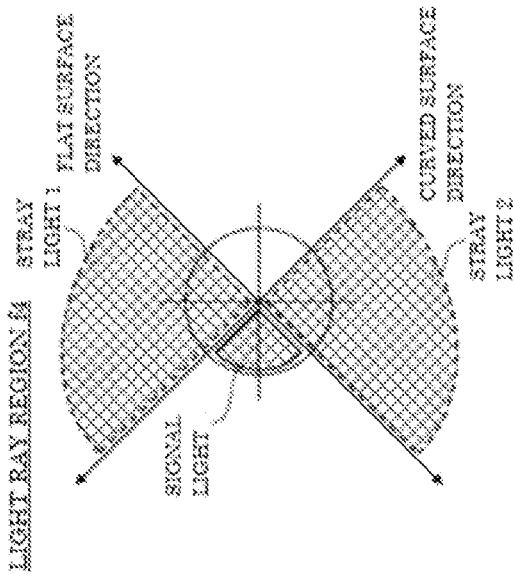
Figure 7C:
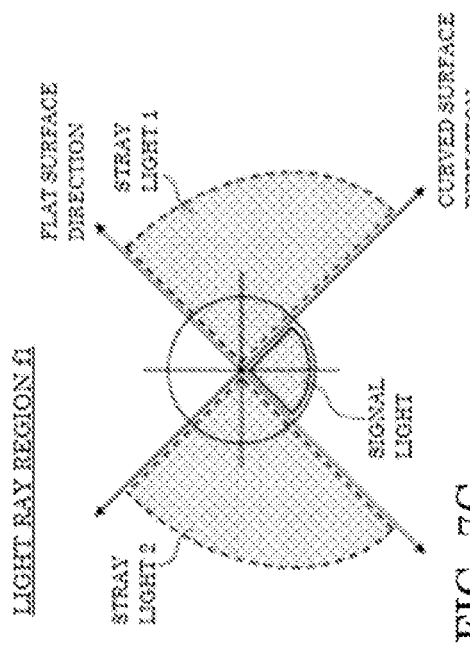
Figure 7D:
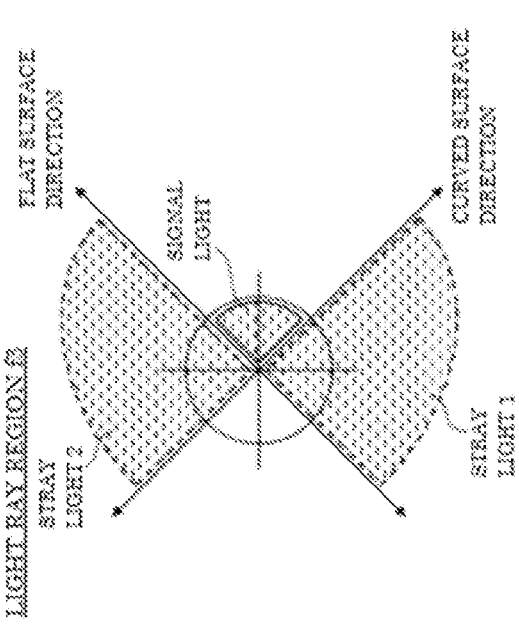

In this case, signal light passing through light ray regions f1 to f4 are distributed as shown in FIG. 6B on the light receiving surface. Stray light 1 passing through light ray regions f1 to f4 is distributed on the light receiving surface as shown in FIG. 6C. Stray light 2 passing through light ray regions f1 to f4 is distributed on the light receiving surface as shown in FIG. 6D. FIGS. 6B to 6D illustrate circles showing the sizes of the beam diameters of the signal lights. As shown in FIGS. 6C and 6D, stray lights 1 and 2 have larger circles than those of the signal light.

When the signal light and stray lights 1 and 2 on the light receiving surface of fluorescence detector 111 are taken out for the respective light ray regions, the respective lights are distributed as shown in FIGS. 7A to 7D. In this case, signal lights passing through the respective light ray regions are not superposed with any of stray light 1 and stray light 2 passing through these light ray regions. Thus, when a configuration is provided in which the signal light and stray lights 1 and 2 passing through the respective light ray regions are dispersed in different directions so that only the signal light is received by a sensor, the sensor can receive only the signal light, thus suppressing the stray light from entering. This can consequently prevent a deteriorated detection signal due to stray light.

As described above, only the signal light can be extracted by dispersing lights passing through light ray regions f1 to f4 to separate the lights on the light receiving surface. Embodiment 1 is made based on this principle.

Figure 8A:
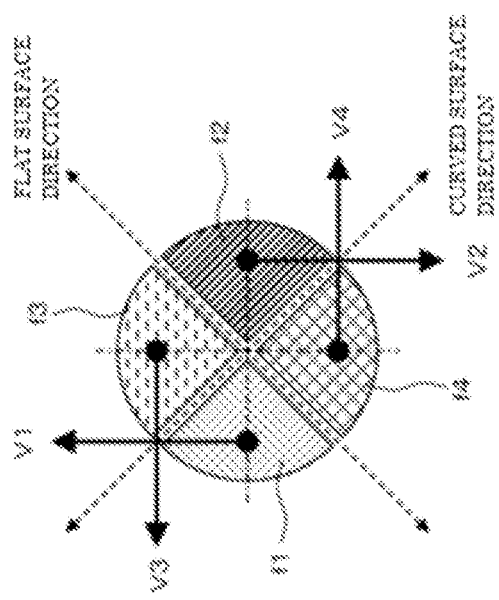
FIGS. 8A and 8B illustrate a vector given in the fluorescence traveling direction according to the technique principle of Embodiment 1 and illustrate a fluorescence irradiation region on a light receiving surface.

FIG. 8A illustrates vectors given in the traveling directions of fluorescence passing through the respective light ray regions in order to separate fluorescence passing through light ray regions f1 to f4 (signal light and stray lights 1 and 2) on plane P0.

When vectors V1 to V4 are given, the traveling directions of the fluorescence passing through light ray regions f1 to f4 change, respectively. The directions of vectors V1 to V4 are inclined by 45 degrees to the flat surface direction and the curved surface direction and are all different. Vectors V1 to V4 have an identical size. The sizes of vectors V1 to V4 are defined as an angle to fluorescence traveling directions (traveling directions when anamorphic lens receives light) before these vectors are given.

Figure 8B:
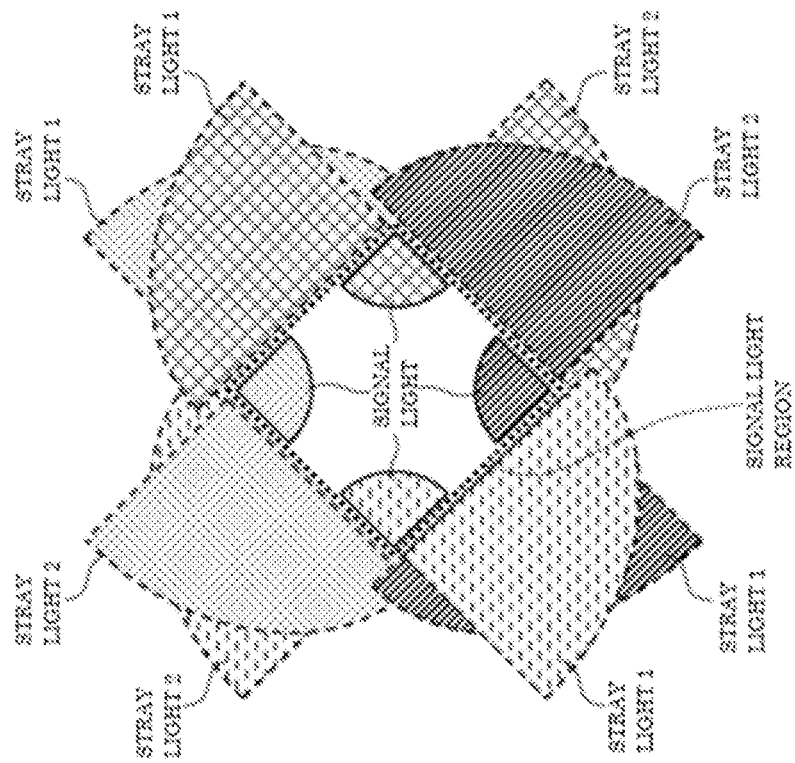

As shown in FIG. 8A, when the traveling directions change, fluorescence passing through light ray regions f1 to f4 (signal light and stray lights 1 and 2) is irradiated on the light receiving surface as shown in FIG. 8B. By adjusting vectors V1 to V4, signal light and stray lights 1 and 2 passing through the respective light ray regions can be distributed on the light receiving surface as shown in FIG. 8B. In this case, irradiation regions of fluorescence passing through light ray regions f1 to f4 (signal light) are positioned at apex angles of a rectangular shape (signal light region) including only these four irradiation regions.

As described above, based on the principle shown in FIG. 5A to FIG. 8B, the light receiving surface of fluorescence detector 111 can have thereon a signal light region including only a fluorescence (signal light) irradiation region. Thus, by allowing this region to include a sensor for receiving fluorescence (signal light), only fluorescence generated from a sample can be received.

FIGS. 9A to 9C illustrate a configuration example of spectral element 110. FIG. 9A illustrates a configuration example in the case where spectral element is configured by a hologram element having a diffraction pattern. FIGS. 9B and 9C illustrate a configuration example in the case where spectral element is configured by a multifaceted prism. FIGS. 9A and 9C are a top view illustrating spectral element 110 seen from anamorphic lens 109.

In the case of configuration example shown in FIG. 9A, spectral element is formed by a transparent plate having a square profile in which a light incidence plane has a blaze-type diffraction pattern (diffraction hologram). Spectral element 110 has a light incidence plane divided to four diffraction regions H11 to H14. Spectral element 110 is provided so that diffraction regions H11 to H14 respectively receive fluorescence passing through light ray regions f1 to f4 of FIG. 8A.

Diffraction regions H11 to H14 cause +primary diffraction light to be generated from fluorescence entering the respective diffraction regions. The +primary diffraction light of the fluorescence having entered diffraction regions H11 to H14 is diffracted in a direction shown by arrows of a solid line (V1 to V4. Diffraction given by diffraction regions H11 to H14 to the fluorescence has directions and magnitudes shown by vectors V1 to V4. The traveling directions of the +primary diffraction light generated by diffraction regions H11 to H14 are obtained by applying vectors V1 to V4 in the traveling directions of fluorescence before the fluorescence is received by the respective diffraction regions.

The directions of vectors V1 to V4 are set depending on the directions of diffraction patterns set in the respective diffraction regions. The magnitudes of vectors V1 to V4 are set depending on the pitches of the diffraction patterns set in the respective diffraction regions. Diffraction regions H11 to H14 have the same diffraction efficiency.

In the case of the configuration examples shown in FIGS. 9B and 9C, spectral element 110 is formed by a transparent body (multifaceted prism) in which a light-emitting plane is flat and light incidence planes are inclined in different directions to one another at four inclined planes L11 to L14. The traveling directions of fluorescence entering inclined planes L11 to L14 are obtained, as in the case of FIG. 9A, by applying vectors V1 to V4 in the traveling directions of fluorescence before the fluorescence is received by the respective diffraction regions by the refraction action during the light receipt by the respective inclined planes.

FIGS. 9D to 9F illustrate a configuration example of a sensor provided on the light receiving surface of fluorescence detector 111.

In the case of the configuration example shown in FIG. 9D, four sensors S11 to S14 having a triangular shape are provided to receive the respective lights positioned within the signal light regions shown in FIG. 8B. Controller determines whether or not malarial parasites are positioned at an excitation light spot position based on the addition signal added with the detection signals of sensors S11 to S14.

In the case of the configuration example shown in FIG. 9E, sensor S15 that has substantially the same rectangular shape as the shape of the signal light region shown in FIG. 8B and that has hole S15a near the center is provided in the signal light region. In the case of the configuration example shown in FIG. 9F, sensor S16 that has substantially the same rectangular shape as the shape of the signal light region is provided in the signal light region. In the case of the configuration examples of FIGS. 9E and 9F, controller 205 determines whether or not malarial parasites are positioned at an excitation light spot position based on the detection signal of the sensor.

As described above, according to Embodiment 1, the light receiving surface of fluorescence detector 111 has thereon irradiation regions of fluorescence (signal light) as shown in FIG. 8B. By placing sensors in signal light regions formed by these irradiation regions as shown in FIGS. 9D to 9F, only fluorescence (signal light) generated from a sample can be received. This can consequently provide an accurate measurement of the sample while suppressing an influence by autofluorescence.

The effect by the above principle may be achieved by a relation as shown in FIG. 5A in which focal line position (P13) by the convergence of stray light 1 in the flat surface direction is closer to anamorphic lens 109 than signal light convergence position (P01) and focal line position (P22) by the convergence of stray light 2 in the curved surface direction is farther away from anamorphic lens 109 than signal light convergence position (P01). Specifically, so long as this relation is satisfied, the signal light and stray lights 1 and 2 are distributed as shown in FIG. 8B as described above. Thus, the signal light and stray lights 1 and 2 on the light receiving surface of fluorescence detector 111 can be prevented from being superposed to one another. In other words, so long as this relation is satisfied, the effect based on the above principle may be achieved even when focal line position (P13) is closer to the light receiving surface than focal line position (P02) or when focal line position (P22) is closer to the light receiving surface than focal line position (P03).

For example, when a position at which autofluorescence (stray lights 1 and 2) occurs in the optical axis direction of excitation light entering biosensor substrate 10 is closer to the position of a sample generating fluorescence, convergence position (P11, P21) is closer to convergence position (P01) in FIG. 5A. In this case, in order to position autofluorescence (stray lights 1 and 2) at the outside of the signal light region as shown in FIG. 8B, focal line position (P13) may be closer to anamorphic lens 109 than convergence position (P01) and focal line position (P22) may be farther away from convergence position (P01) as described above.

Embodiment 2

In Embodiment 1, spectral element 110 shown in FIGS. 9A and 9C as used. In Embodiment 2 on the other hand, spectral element 110 is substituted with spectral element 113. The following section will describe a technical principle for using spectral element 113 with reference to FIG. 10A to FIG. 11D.

FIG. 10A illustrates a fluorescence convergence status. FIG. 10A also illustrates spectral element 113 of Embodiment 2 in the convergence status as in FIG. 5A. Spectral element 113 is provided between focal line position (P13) by the convergence of stray light 1 in the flat surface direction and focal line position (P02) by the convergence of signal light in the curved surface direction. Embodiment 2 uses anamorphic lens 109 shown in FIG. 10B as in Embodiment 1.

As described above, stray light 1 has focal line position (P13) that changes in the optical axis direction depending on an autofluorescence depth position in the optical axis direction. Thus, spectral element 113 desirably provided closer to focal line position (P02) of signal light as much as possible. In the case of Embodiment 2, when focal line position (P13) of stray light 1 is closer to convergence position (P01) than focal line position (P02) of signal light, the signal light cannot be separated from the stray light. Specifically, in Embodiment 2, when focal line position (P13) of stray light 1 is farther away from convergence position (P01) with regard to focal line position (P02) of the signal light, an action is achieved to remove the stray light. Thus, a range within which stray light is removed is limited than in the case of Embodiment 1.

FIG. 10C is a perspective view illustrating the shape of spectral element 113. FIG. 10D illustrates spectral element 113 seen from the light incidence side. Spectral element 113 is formed by a transparent body (multifaceted prism) in which a light-emitting plane is flat and light incidence planes are respectively inclined in different directions at two inclined planes.

A boundary between inclined planes L21 and L22 forms a straight line parallel to the flat surface direction when seen from the light incidence side. The traveling directions of fluorescences entering inclined planes L21 and L22 is obtained by applying vectors Va and Vb in the traveling direction of fluorescence before the fluorescence is received by the respective inclined planes by the refraction action during the light receipt by the respective inclined planes. The directions of vectors Va and Vb are parallel to the curved surface direction and are different from each another. Vectors Va and Vb have the same magnitude. The magnitudes of Vectors Va and Vb are defined as an angle to the traveling direction of fluorescence (the traveling direction when fluorescence is received by anamorphic lens 109) before these vectors are given.

Figures 11A, 11B, 11C, 11D:
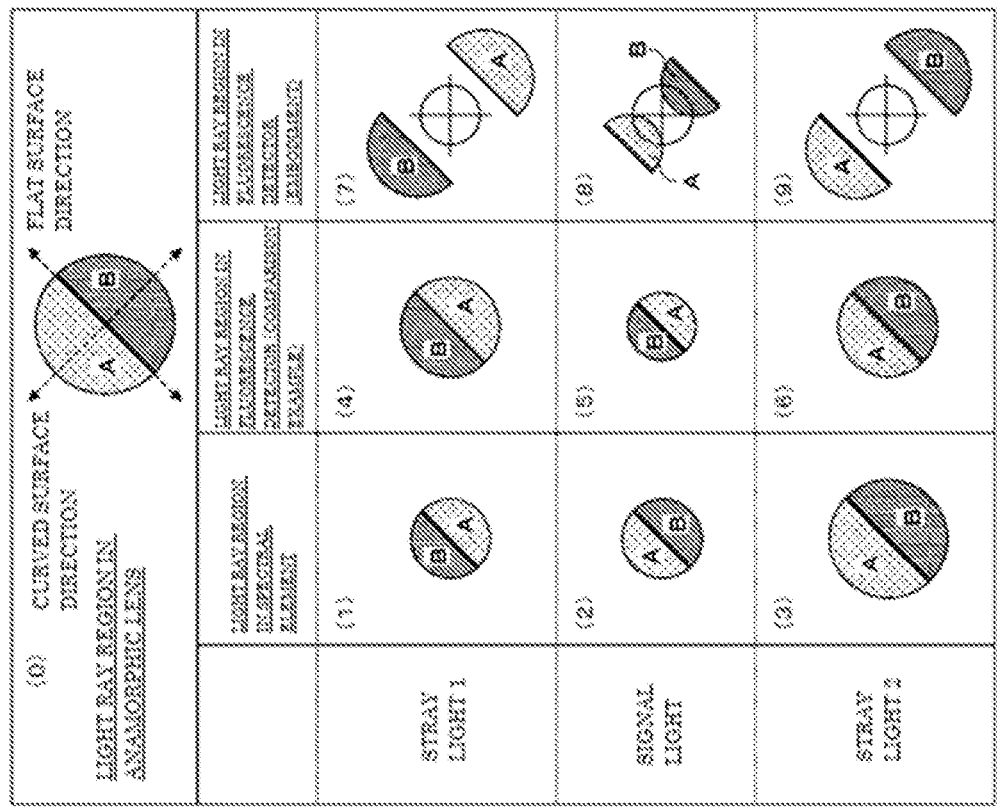
FIGS. 11A to 11D are a diagram schematically illustrating the status of a fluorescence light ray region according to Embodiment 2, a diagram illustrating superposed light ray regions in the case of a comparison example, and a diagram illustrating a fluorescence light ray region on the light receiving surface.

FIG. 11A schematically illustrates the statuses of fluorescence light ray regions at the respective positions of anamorphic lens 109, spectral element 113, and fluorescence detector 111. As shown in FIG. 11A(0), an upper-left light ray region and a lower-right light ray region obtained by halving light ray regions of fluorescence (signal light and stray lights 1 and 2) when fluorescence is received by anamorphic lens 109 along the straight line parallel to the flat surface direction will be referred to for convenience as light ray region A and light ray region B, respectively. FIGS. 11A(1) to 11A(9) illustrate how light ray regions A and B set for fluorescence (signal light and stray lights 1 and 2) are distributed in spectral element 113 and fluorescence detector 111.

The following section will describe, with reference to the fluorescence convergence statuses of FIG. 11A and FIG. 10A, the statuses of light ray regions at the respective positions.

First, the following section will describe the statuses of light ray regions when fluorescence (signal light and stray lights 1 and 2) is received by spectral element 113.

When fluorescence (stray light 1) passes through anamorphic lens 109 and is subsequently received by spectral element 113, fluorescence (stray light 1) is converged in an order of a curved surface direction and a flat surface direction to thereby form a focal line. This focal line forms an elongate shape in the flat surface direction and the curved surface direction, respectively. As a result, light ray regions A and B shown in stray light 1 shown in FIG. 11A(0) pass through focal line position (P12) shown in FIG. 10A and is subsequently inverted along a straight line parallel to the flat surface direction as a symmetry axis. Next, light ray regions A and B of stray light 1 passes through focal line position (P13) shown in FIG. 10A and is subsequently inverted along a straight line parallel to the curved surface direction as a symmetry axis. During this, no change is caused in the statuses of light ray regions A and B of stray light 1. Thus, light ray regions A and B of stray light 1 at spectral element 113 are in the status show in FIG. 11A(1).

During a period from the passage of fluorescence (signal light) through anamorphic lens 109 to the incidence on spectral element 113, both of the flat surface direction and the curved surface direction do not form a focal line. Thus, light ray regions A and B of stray light at spectral element 113 are in the status shown in FIG. 11A(2) as in the status shown in FIG. 11A(0).

As in signal light, during a period from the passage of fluorescence (stray light 2) through anamorphic lens 109 to the incidence on spectral element 113, both of the flat surface direction and the curved surface direction do not form a focal line. Thus, light ray regions A and B of stray light 2 at spectral element 113 are in the status shown in FIG. 11A(3) as in the status shown in FIG. 11A(0).

In order to describe the function and action of spectral element 113, the following section will firstly describe fluorescence (signal light and stray lights 1 and 2) in what status are received by fluorescence detector 111 when no spectral element 113 is provided (comparison example).

During a period from the passage of fluorescence (stray light 1) through spectral element 113 to the incidence on fluorescence detector 111, both of the flat surface direction and the curved surface direction do not form a focal line. Thus, light ray regions A and B of stray light 1 at fluorescence detector 111 are in the status shown in FIG. 11A(4) as in the status shown in FIG. 11A(1).

During a period from the passage of fluorescence (signal light) through spectral element 113 to the incidence on fluorescence detector 111, a focal line is formed in the curved surface direction but no focal line is formed in the flat surface direction. Thus, after light ray regions A and B of stray light shown in FIG. 11A(2) pass through focal line position (P02) shown in FIG. 10A, light ray regions A and B of stray light shown in FIG. 11A(2) are inverted along the straight line parallel to the flat surface direction as a symmetry axis. Thus, light ray regions A and B of stray light at fluorescence detector 111 are in the status shown in FIG. 11A(5).

During a period from the passage of fluorescence (stray light 2) through spectral element 113 to the incidence on fluorescence detector 111, both of the flat surface direction and the curved surface direction do not form a focal line. Thus, light ray regions A and B of stray light at fluorescence detector 111 are in the status shown in FIG. 11A(6) as in the status shown in FIG. 11A(3).

Next, the following section will describe that fluorescence (signal light and stray lights 1 and 2) in what status is received by fluorescence detector 111 in the case where spectral element 113 is provided as in Embodiment 2. In this case, when fluorescence (signal light and stray lights 1 and 2) passes through an upperleft light ray region and a lower-right light ray region of spectral element 113, the traveling direction of the fluorescence (signal light and stray lights 1 and 2) is given, by the spectral action of spectral element 113 shown in FIG. 10D, with a upper left direction component and a lower right direction component, respectively.

The traveling direction of stray light 1 passing through light ray regions A and B shown in FIG. 11A(1) is given with a lower right direction component and an upper left direction component, respectively. As a result, light ray regions A and B of stray light 1 at fluorescence detector 111 are respectively moved from the status of the comparison example shown in FIG. 11A(4) in the lower right direction and the upper left direction, thus resulting in the status shown in FIG. 11A(7).

The traveling direction of the signal light passing through light ray regions A and B shown in FIG. 11A(2) is added with an upper left direction component and a lower right direction component, respectively. As a result, light ray regions A and B of stray light 1 at fluorescence detector 111 are respectively moved from the status of the comparison example shown in FIG. 11A(5) in the upper left direction and the lower right direction, thus resulting in the status shown in FIG. 11A(8).

The traveling direction of the signal light passing through light ray regions A and B shown in FIG. 11A(3) is added with an upper left direction component and a lower right direction component, respectively. As a result, light ray regions A and B of stray light 2 at fluorescence detector 111 are respectively moved from the status of the comparison example shown in FIG. 11A(6) in the upper left direction and the lower right direction, thus resulting in the status shown in FIG. 11A(9).

The distribution of light ray regions A and B of fluorescence (signal light and stray lights 1 and 2) at fluorescence detector 111 also may be considered as follows.

FIGS. 11B and 11C illustrate that light ray regions of fluorescence (signal light and stray lights 1 and 2) at fluorescence detector 111 are superposed in the case of the comparison example. FIG. 11B illustrates the distribution of only the fluorescence passing through an upper left light ray region when being received by spectral element 113. FIG. 11C illustrates the distribution of only the fluorescence passing through a lower right light ray region when being received by spectral element 113.

As shown in FIG. 11B, light ray region B of stray light 1, light ray region A of stray light 2, and light ray region A of the signal light are all moved in the direction of vector Va (upper left direction) by the spectral action of spectral element 113. As shown in FIG. 11C, light ray region A of stray light 1, light ray region B of stray light 2, and light ray region B of the signal light are all moved in the direction of vector Vb (lower right direction) of the spectral action of spectral element 113.

The fluorescence light ray regions thus moved are in the status shown in FIG. 11D. Then, a position close to the center of fluorescence detector 111 can have a signal light region in which only light ray regions A and B of stray light are distributed.

Figure 12A:
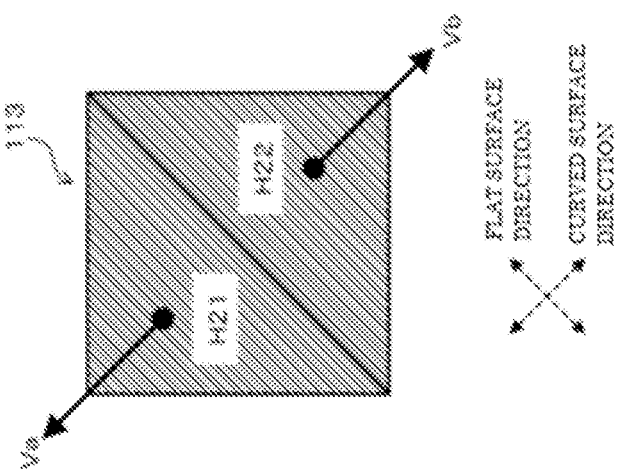
FIGS. 12A to 12C are a diagram illustrating another configuration of the spectral element according to Embodiment 2 and a diagram illustrating a configuration example of a sensor provided on the light receiving surface of the fluorescence detector.

FIG. 12A illustrates another configuration example of spectral element 113. Spectral element 113 of this case is configured by a transparent plate having a square profile in which a light incidence plane has a blaze-type diffraction pattern (diffraction hologram). The light incidence plane of spectral element 113 is divided into two diffraction regions H21 and H22. This case is similar in the case of the configuration example of spectral element 113 shown in FIGS. 10C and 10D in that light ray regions A and B of the fluorescence (signal light and stray lights 1 and 2) can be distributed as shown in FIG. 11D.

Figure 12B:
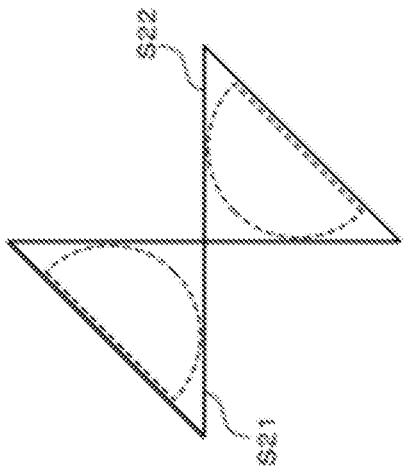
Figure 12C:
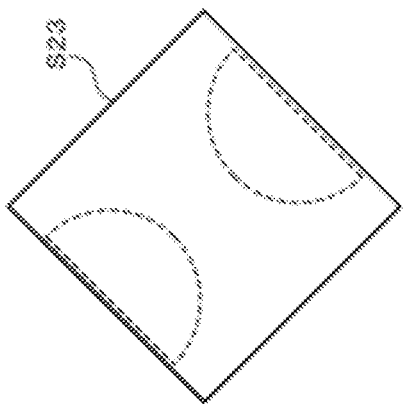

FIGS. 12B and 12C illustrates a configuration example of a sensor provided on the light receiving surface of fluorescence detector 111.

In the case of configuration example shown in FIG. 12B, two sensors S21 and S22 having a triangular shape are provided to receive a signal light positioned in the signal light region shown in FIG. 11D. In this case, controller determines whether or not malarial parasites are positioned at an excitation light spot position based on an addition signal added with the detection signals of sensors S21 and S22. In the case of the configuration example shown in FIG. 12C, the signal light region includes sensor S23 having substantially the same rectangular shape as the shape of the signal light region shown in FIG. 11D. In this case, controller 205 determines, based on the detection signal of sensor S23, whether or not malarial parasites are positioned at the excitation light spot position. By placing sensors S21, S22, and S23 as described above, fluorescence (signal light) generate from a sample can be similarly received in Embodiment 2. Thus, the sample can be accurately measured while suppressing the influence by autofluorescence for example.

In Embodiment 2, as shown in FIGS. 13A-1 and 13B-1, the fluorescence light ray region in fluorescence detector 111 in the case of the comparison example is moved in the upper left direction and the lower right direction (i.e., the directions of vectors Va and Vb by the spectral action of spectral element 113). As a result, in Embodiment 2, the light ray region is positioned as shown in FIG. 13C-1.

However, the directions of vectors Va and Vb are not limited to the upper left direction and the lower right direction and also may be a left direction and a right direction as shown in FIGS. 13A-2 and 13B-2 or may be an upper direction and a lower direction as shown in FIGS. 13A-3 and 13B-3. In this case, FIGS. 13C-2 and 13C-3, the neighborhood of the center can have a rectangular signal light region in which only light ray regions A and B of stray light are distributed.

The directions of vectors Va and Vb are both parallel to the flat surface direction or the curved surface direction. The magnitudes of vectors Va and Vb may be different from each other. Alternatively, any one of inclined planes L21 and L22 of spectral element 113 shown in FIG. 10D may be a flat plant not including inclination and a refraction action can be applied only to any of fluorescences received by spectral element 113 that is received by inclined planes L21 and L22. Similarly, any one of diffraction regions H21 and H22 of spectral element 113 shown in FIG. 12A may be a region not having a diffraction pattern and a diffraction action may be applied only to any of fluorescence received by spectral element 113 that is received by diffraction regions H21 and H22. Signal lights passing through light ray regions A and B are not always required to be separated on the light receiving surface and may be superposed to each other. As described above, spectral element 113 may be configured so that stray lights 1 and 2 are prevented from being superposed with signal light on the light receiving surface of fluorescence detector 111.

As described above, embodiments of the present invention have been described. However, the present invention is not limited to the above embodiments in any way. Other modification other than the above embodiment can be made in the present invention.

For example, in the above embodiments, well 13 stores therein erythrocytes to determine whether or not the erythrocytes are infected with malarial parasites. However, a sample stored in well 13 and a phenomenon to be determined are not limited to this.

For example, a cell expressing a specific gene or a cell including biological material (e.g., nucleic acid, protein, lipid) larger or smaller than a normal amount may be detected as a specific cell from among a variety of cell groups. Alternatively, a normally functioning cell may be detected as a specific cell from among a cell group. This is used, for example, for the purpose of detecting a normally-differentiated cell for the guide of an iPS cell or an ES cell from an undifferentiated status to a differentiated status. The specific cell as described above may be a cell existing in a natural world or an artificially-processed cell. Cells existing in a natural world include, in a non-limited manner, a pathogenic cell, a lesion cell, a cell infected with pathogens or pathogenic living organism, a mutated cell, a unknown cell having a specific characteristic for example. An artificial processing includes, in a not-limited manner, a physical processing (e.g., electromagnetic wave irradiation), a chemical processing (e.g., agent processing), and a genetic engineering processing (e.g., gene recombination processing) for example.

Among the artificial processings as described above, a processing for which an influence on a cell is known also can be applied to a cell group and a cell not showing the influence or a cell showing the influence in a stronger manner can be detected as a specific cell. For example, a cell showing a resistance or high sensitivity to an agent processing may be detected as a specific cell.

The type of a cell group is also not particularly limited. In addition to a group of a single-cell living organism, the invention also can be applied to a cell group derived from a multicell living organism. A cell derived from a multicell living organism includes, for example, a cell obtained from a normal tissue or a pathological tissue of a living organism or a cultured cell derived from these cells. A living organism from which these cells are obtained is also not particularly limited. For example, a cell may be extracted from animals or plants. More specifically, a cell extracted from vertebrate animal (mammals and birds in particular), a cell extracted from insects, and a cell cultured from plants may be detected for example. However, the invention is not limited to such cells. Alternatively, a single cell group may include a plurality of types of cells.

In the above embodiment, the upper side of well 13 may have a cover during the rotation of biosensor substrate 10 by rotation device 123. This can consequently prevent the undesired leakage, evaporation, or move of sample from well 13 (unintended leakage).

Figure 14A:
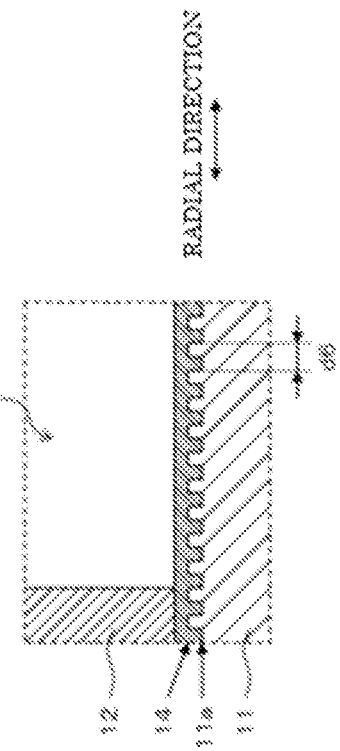
FIGS. 14A to 14C illustrate another configuration example of a well according to an embodiment.
Figure 14C:
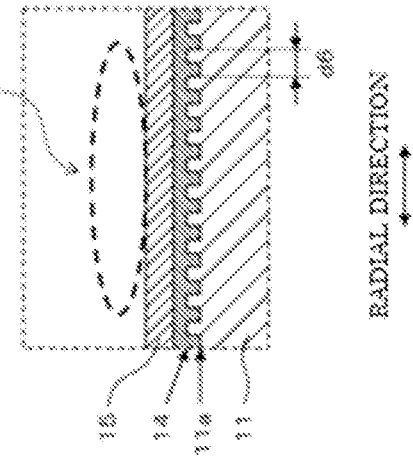
Figure 14B:
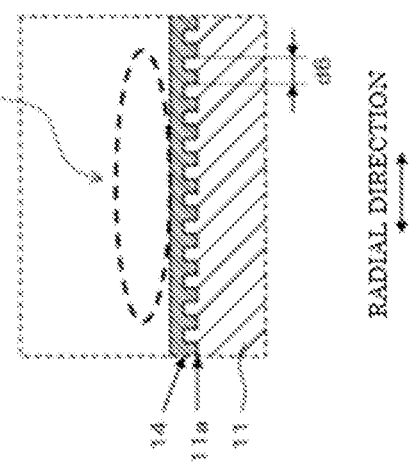

In the above embodiment, a configuration has been described in which well layer 12 provided on reflection film 14 includes well 13 having bottom face 13a. However, another configuration also may be used in which bottom face 13a of well 13 constitutes the upper face of reflection film 14. Specifically, as shown in FIG. 14A, well 13 is configured by a penetrating hole of well layer 12 and is formed on reflection film 14. Another configuration not using well 13 as shown in FIG. 14B also may be used in which a sample is fixed on reflection film 14. Another configuration as shown in FIG. 14C also may be used in which a sample is fixed on layer 15 formed on reflection film 14. In the case of the configurations shown in FIGS. 14B and 14C, a position at which a sample is fixed may have a structure providing some absorbing action. For example, a molecule layer rich in a hydroxyl (OH) group may be provided on reflection film or on layer 15 in the case of FIG. 14C to thereby promote the absorption of a sample.]

Figure 15A:
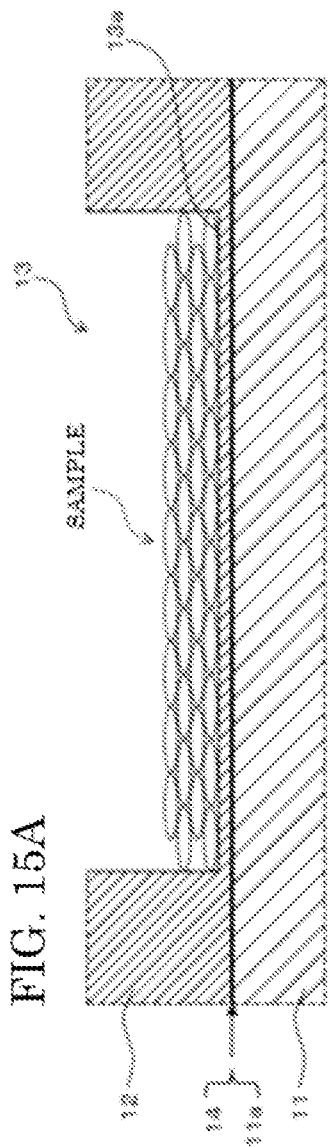
FIGS. 15A to 15C are a diagram illustrating samples superposed in a well according to an embodiment and a method of adjusting a fluorescence detection position.

In the above embodiment, excitation light was converged at samples arranged to be parallel on bottom face 13a of well 13 so that fluorescence from these samples is detected. However, when samples are superposed in well 13 as shown in FIG. 15A, excitation light may be converged at a layer other than a layer including a sample contacting with bottom face 13a (a layer just above the contacting layer) so that the fluorescence from the sample of the layer may be detected while being discriminated from the fluorescence of samples of other layers. As a result, fluorescence can be detected not only from a sample contacting with bottom face 13a but also from samples other than those in well 13, thus providing a fluorescence detection processing having an improved throughput.

A method for conversing excitation light at a layer other than a layer including a sample contacting with bottom face 13a (a layer just above the contacting layer) includes a method of adjusting an offset voltage outputted to objective lens actuator 122 for example. Another method is to set an excitation light convergence position is set farther away from a laser light convergence position for generating a servo signal in a configuration in which a semiconductor laser and emitting laser light for generating a servo signal and a semiconductor laser emitting excitation light are provided, respectively.

Figure 15B:
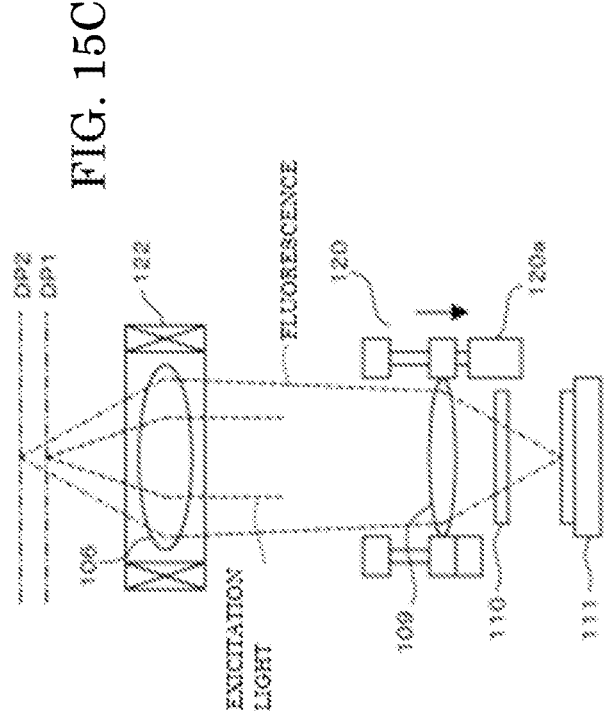
Figure 15C:
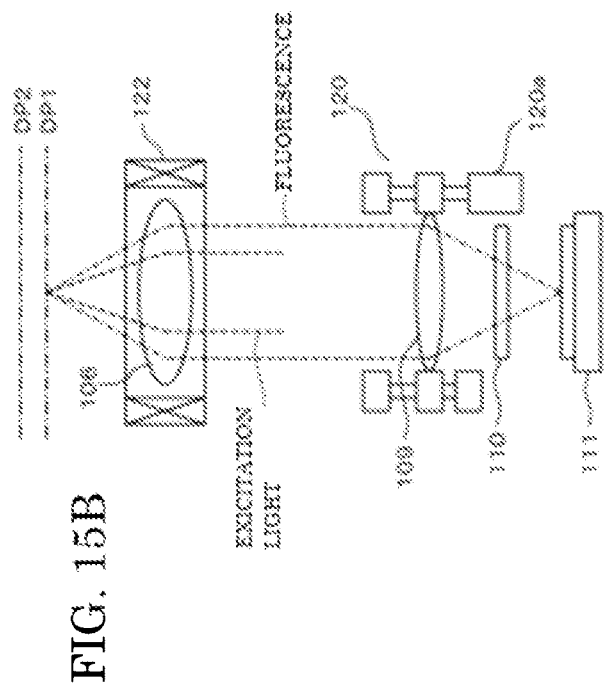

A method of acquiring, as signal light, fluorescence from a layer other than a layer including a sample contacting with bottom face 13a (a layer just above the contacting layer) includes a method of shifting anamorphic lens 109 in the optical axis direction of the fluorescence. In this case, as shown in FIGS. 15B and 15C, fluorescence detection device 1 includes lens actuator 120 that supports anamorphic lens 109 and that allows anamorphic lens 109 to be movable in the optical axis direction. Lens actuator 120 has motor 120a for driving anamorphic lens 109. When lens actuator 120 is controlled to shift anamorphic lens 109 in the optical axis direction, only fluorescence detector 111-side focal point position can be adjusted while leaving the focal point position of excitation light in biosensor substrate 10 as it is. For example, when anamorphic lens 109 is dislocated from the status as shown in as shown in FIG. 15B in which the fluorescence (signal light) from depth position DP1 is irradiated to a signal light region on the light receiving surface of fluorescence detector 111 to a position of FIG. 15C, fluorescence (signal light) from depth position DP2 deeper than depth position DP1 is irradiated to the signal light region on the light receiving surface of fluorescence detector 111. When anamorphic lens 109 is dislocated from the status of FIG. 15B in an opposite direction to FIG. 15C, fluorescence (signal light) from a position shallower than depth position DP1 is irradiated to the signal light region on the light receiving surface of fluorescence detector 111. By adjusting the position of anamorphic lens 109 as described above, fluorescence from a layer as a detection target can be detected even when samples are superposed as shown in FIG. 15A.

According to this configuration, there is no need to dislocate the focal point position of the excitation light. Thus, a stable focus control can be provided based on a detection signal from light detector 108 receiving reflected excitation light. However, excitation light is converged at reflecting surface 11a. Thus, excitation light is expanded in a direction away from bottom face 13a of well 13. Thus, expanded excitation light is irradiated to a sample of a layer away from bottom face 13a of well 13, thus causing a proportionally-reduced fluorescence. When samples are included in an increased number of layers, the focal point position of the excitation light may be shifted from reflecting surface 11a in the direction of well 13 by appropriately adjusting an offset voltage as described above. By superposing pieces of information from a plurality of layers thus obtained, the information can be handled as three-dimensional distribution information. Thus, many samples can be inspected even through a small amount of samples.

In the above embodiment, PBS 102 and ¼ wavelength plate 104 were used. However, ¼ wavelength plate 104 may be omitted and PBS 102 may be substituted with beam splitter (BS).

In the above embodiment, excitation light emitted from semiconductor laser 101 is irradiated to reflection film 14 to generate a servo signal for controlling objective lens 106 and is irradiated to a sample to generate fluorescence therefrom. However, the invention is not limited to this. Thus, fluorescence detection device 1 may include semiconductor laser emitting laser light for generating a servo signal and semiconductor laser emitting excitation light for generating fluorescence separately.

In Embodiment 1, spectral element 110 was provided between anamorphic lens 109 and fluorescence detector 111. However, spectral element may be provided between dichroic prism 105 and anamorphic lens 109. When spectral element 110 has wavelength selectivity providing a spectral action according to which no spectral action is given to excitation light and only a spectral action is given to fluorescence, spectral element 110 as described above may be provided between objective lens 106 and dichroic prism 105.

In Embodiment 1, a configuration was used as shown in FIG. 8B in which signal light irradiation regions were separated from each other on the light receiving surface. However, signal light irradiation regions are not always required to be separated and also may be superposed to each other.

In Embodiment 1, the light incidence plane of spectral element 110 had a blaze-type diffraction pattern. However, the invention is not limited to this. The light incidence plane of spectral element 110 may have a step-type diffraction pattern. In this case, the diffraction actions by diffraction regions H11 to H14 cause +primary diffraction light and −primary diffraction light from the fluorescence received by the respective diffraction regions. Then, any one of +primary diffraction light and −primary diffraction light of the signal light is included in the signal light region and the other is introduced to the outside of the signal light region. Thus, the amount of fluorescence generated from the sample that is received by the sensor is a half of that in Embodiment 1. Thus, from the viewpoint of the amount of received fluorescence, a blaze-type diffraction pattern is desirably formed in spectral element 110 as in Embodiment 1.

In Embodiment 2, spectral element 113 was provided between focal line position (P13) by the convergence of stray light 1 in the flat surface direction and focal line position (P02) by the convergence of signal light in the curved surface direction. However, spectral element 113 also may be provided between focal line position (P12) by the convergence of stray light 1 in the curved surface direction and focal line position (P13) by the convergence of stray light 1 in the flat surface direction. In this case, in contrast with the case of FIG. 10A, an opposite positional relation is caused between focal line position (P13) by the convergence of stray light 1 in the flat surface direction and spectral element 113. However, the distributions of the light ray regions at the respective positions are totally the same as FIG. 11A.

In the above embodiment, dichroic prism 105 was used to separate fluorescence from reflected excitation light from biosensor substrate 10. However, other methods also may be used to separate fluorescence from reflected excitation light.

Figure 16:
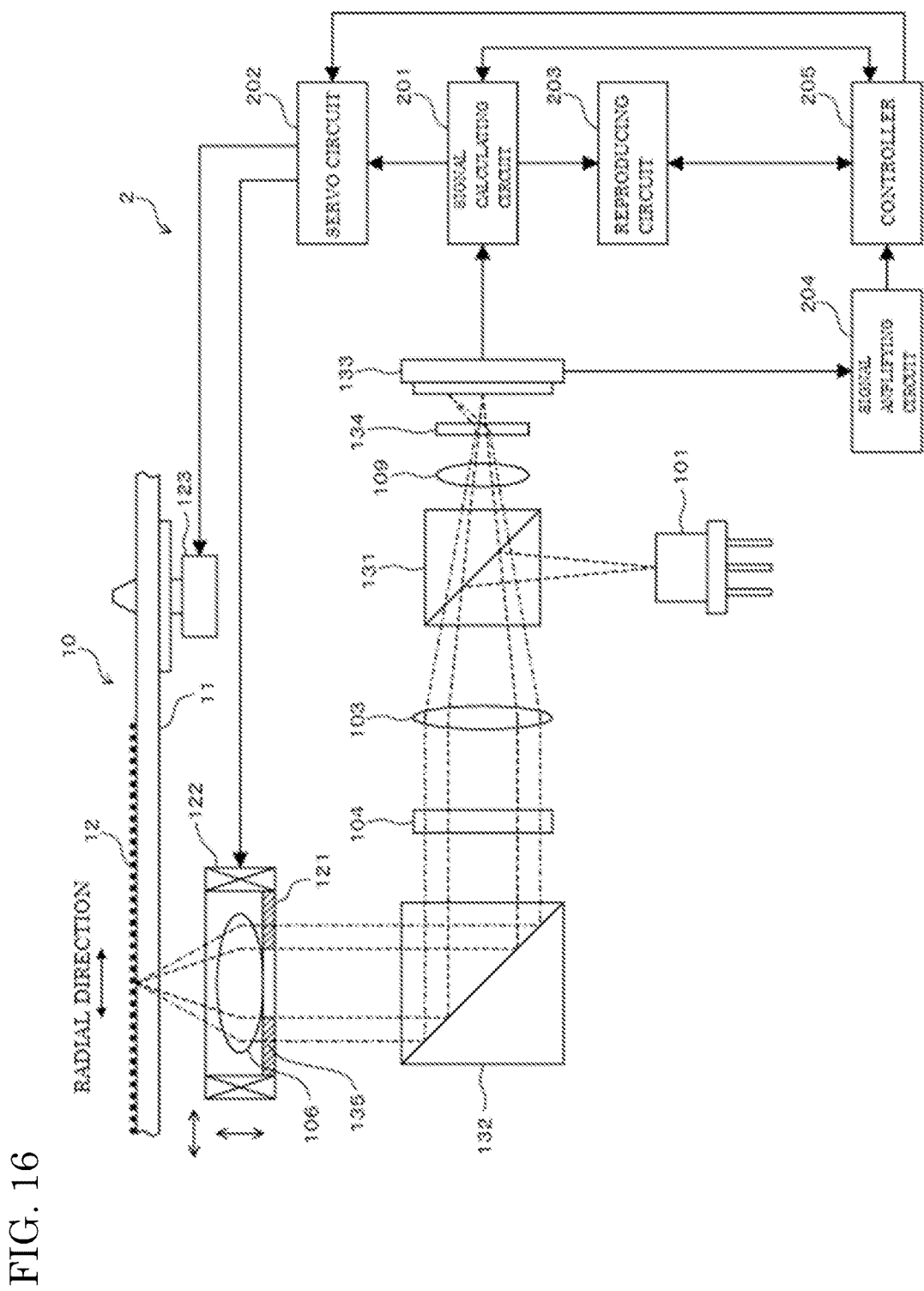
FIG. 16 illustrates another configuration of the fluorescence detection device according to an embodiment.

FIG. 16 illustrates the configuration of fluorescence detection device 2 when another method is used to separate fluorescence from reflected excitation light. Fluorescence detection device 2 is configured so that PBS 102 is substituted with PBS 131, dichroic prism 105 is substituted with reflection mirror 132, light detector 108 is substituted with light detector 133, and anamorphic lens 107 and fluorescence detector 111 are omitted. Furthermore, spectral element 110 or spectral element 113 of the above embodiment are omitted and spectral element 134 is provided between anamorphic lens 109 and light detector 133. Furthermore, aperture 112 is omitted holder 121 has circular aperture 135 provided at reflection mirror 132 of objective lens 106. PBS 131 is different from PBS 102 in that PBS 131 is composed of a wavelength-selective PBS that acts on excitation light and that does not act on fluorescence. Specifically, excitation light passes through or reflects PBS 131 depending on a polarization direction. Fluorescence entirely passes through PBS 131 regardless of the polarization direction. Aperture 135 also has a wavelength-selectivity according to which a specific periphery of excitation light is blocked and fluorescence is entirely allowed to pass therethrough.

In this case, as in the above embodiment, excitation light emitted from semiconductor laser 101 is reflected by PBS 131. The reflected excitation light from collimator lens 103 is received by PBS 131 is allowed to pass through PBS 131. The excitation light from reflection mirror 132 is received by aperture and is caused by aperture 135 to have a specific diameter. The fluorescence from objective lens 106 is received by aperture 135 is allowed to pass through aperture 135 and is received by reflection mirror 132. The fluorescence received by reflection mirror 132 is reflected by reflection mirror and is allowed to pass through ¼ wavelength plate 104, collimator lens 103, PBS 131, and anamorphic lens 109.

Spectral element 134 has a wavelength dependence according which no diffraction action is given to reflected excitation light and a diffraction action is given only to fluorescence. Spectral element 134 gives, to fluorescence, a spectral action similar to that by spectral element 110 of Embodiment 1 or spectral element 113 of Embodiment 2. Furthermore, spectral element 34 also gives a spectral action according to which fluorescence received by spectral element 134 is dispersed in the upper direction of FIG. 16 to separate the fluorescence from the reflected excitation light. Based on a difference between a starting point of the reflected excitation light (reflecting surface 11a) and a starting point of the fluorescence (sample) and based on chromatic aberration at an optical member to the reflected excitation light and the fluorescence, the fluorescence is undesirably defocused on the light receiving surface of light detector 133. Spectral element 134 has, in addition to the above-described spectral action, a lens action (diffraction action) to absorb this defocusing. Specifically, spectral element 134 gives a lens action to fluorescence so that the convergence position of the fluorescence from the sample (P01: see FIG. 5A, FIG. 10A) is aligned with the light receiving surface of light detector 133. As a result, the irradiation region as in FIG. 8B or the light ray region as in FIG. 11D is positioned at such a position on the light receiving surface of light detector that is in the upper direction of FIG. 16 than the irradiation position of the reflected excitation light. Then, the light receiving surface of light detector 133 has thereon the tetrameric sensor as shown in FIG. 4 and a sensor for receiving signal light as in the above embodiment in the upper direction of FIG. 16 than the tetrameric sensor.

Light detector 133 outputs a detection signal based on the reflected excitation light to signal calculating circuit 201 and outputs a detection signal based on the fluorescence to signal amplifying circuit 204. As a result, fluorescence detection device 2 also can accurately measure the sample while suppressing the influence by autofluorescence as in the above embodiment.

In the configuration shown in FIG. 16, aperture 135 for defining the beam diameter of excitation light was placed in holder 121. However, the invention is not limited to this. Thus, the aperture also may be provided at the emission side of collimator lens 103 and this aperture may have polarization selectivity and wavelength selectivity. When the aperture is provided at the emission side of collimator lens 103, the light ray of excitation light moving toward objective lens 106 is fixed. Thus, if objective lens 106 is dislocated in the tracking direction in a tracking control for example, then the light ray of the excitation light is undesirably dislocated from the center of objective lens 106, thus causing a risk of excitation light having a deteriorated optical characteristic. In order to avoid this disadvantage, a configuration as shown in FIG. 14 is desirably used in which aperture 135 is provided at the incidence side of objective lens 106 so that aperture 135 and objective lens 106 are moved in an integrated manner.

In the above embodiment, a sample was retained by a disk-like carrier. However, a carrier for retaining a sample is not limited to this. For example, a sample may be retained by a card-like carrier having a square-shaped profile. In this case, the card is configured so that wells and tracks are arranged to form a straight line in one direction. A fluorescence detection device is configured so as to scan the tracks by excitation light while moving the card relative to objective lens 106 in a direction parallel to the tracks.

In addition to the above, an embodiment of the present invention can be appropriately changed in various manners within the scope of the technical concept shown in claims.

What is the claim is:

1. A fluorescence detection device that irradiates a sample holding carrier holding a fluorescently-labeled sample with irradiation light and detects fluorescence yielded from the sample irradiated with the irradiation light,
the fluorescence detection device comprising:
a light source that emits the irradiation light;
an objective lens that converge the irradiation light at the sample on the sample holding carrier;
an astigmatism element for introducing astigmatism to fluorescence having entered the objective lens from the sample holding carrier and having passed through the objective lens;
a spectral element for separating the fluorescence into a plurality of light rays; and
a fluorescence detector for receiving the light ray separated by the spectral element,
wherein the spectral element disperses the fluorescence on a light receiving surface of the fluorescence detector so that fluorescence generated from the sample position is separated from fluorescence generated from a specific depth position other than the sample position, and
the fluorescence detector has a light-receiving section in a region in which the fluorescence generated from the sample position is irradiated and the fluorescence generated from the specific depth region other than the sample position is not irradiated.

2. The fluorescence detection device according to claim 1, wherein
the sample holding carrier comprises a sample accommodation unit for storing the sample and a reflecting surface that is provided closer to the incidence side of the irradiation light than the sample accommodation unit and that reflects a part of the irradiation light, and
the fluorescence detection device further comprises a reflection light detector that receives reflection light of the irradiation light reflected by the reflecting surface.

3. The fluorescence detection device according to any one of claim 2, wherein
the spectral element is configured by a wavelength-selective diffraction element, and
the spectral element receives the fluorescence and reflection light of the irradiation light reflected by the reflecting surface and further gives to the fluorescence a diffraction action for separating, based on a wavelength difference between the fluorescence and the reflection light, the fluorescence and the reflection light from each other.

4. The fluorescence detection device according to any one of claim 2, wherein
The fluorescence detection device further comprises a mechanism that can change positions of the objective lens, the astigmatism element, the spectral element, or the light-receiving section in an optical axis of the fluorescence direction, and
the fluorescence detection device separates and detects fluorescence generated from the sample provided at a different position of the optical axis direction.

5. The fluorescence detection device according to claim 1, wherein
the astigmatism element generates a first focal line by the fluorescence convergence in a first direction and generates a second focal line by the fluorescence convergence in a second direction vertical to the first direction,
the spectral element separates four of the light rays from the fluorescence, and
when an intersection point of two straight lines that are parallel to the first direction and the second direction, respectively, and that intersect to each other is aligned to an optical axis of the fluorescence, four of the light rays are included in four fluorescence regions divided by the two straight lines, respectively.

6. The fluorescence detection device according to claim 5, wherein
the spectral element has a structure that changes traveling directions of four of the light rays so that four of the light rays are respectively irradiated to four apex angles of a square on the fluorescence detector.

7. The fluorescence detection device according to claim 1, wherein
the astigmatism element generates a first focal line by the fluorescence convergence in a first direction and generates a second focal line by the fluorescence convergence in a second direction vertical to the first direction,
the spectral element separates two of the light rays from the fluorescence,
when a straight line parallel to the first direction is aligned to an optical axis of the fluorescence, two of the light rays are included in two fluorescence regions divided by the straight line, respectively, and
the spectral element is provided closer to the objective lens than the objective lens-side focal line among two focal lines generated by the conversion by the astigmatism element of the fluorescence generated from the sample position.

8. The fluorescence detection device according to claim 7, wherein
the spectral element has a structure that changes traveling directions of two of the light rays so that two of the light rays are separated from each other in the second direction.

* * * * *